United States Patent
Oike et al.

(10) Patent No.: US 11,753,429 B2
(45) Date of Patent: Sep. 12, 2023

(54) COBALT COMPLEX, METHOD FOR MANUFACTURING SAME, AND METHOD FOR MANUFACTURING COBALT-CONTAINING THIN FILM

(71) Applicants: TOSOH CORPORATION, Shunan (JP); SAGAMI CHEMICAL RESEARCH INSTITUTE, Ayase (JP)

(72) Inventors: Hiroyuki Oike, Ayase (JP); Teppei Hayakawa, Ayase (JP); Yuki Yamamoto, Ayase (JP); Taishi Furukawa, Ayase (JP); Ken-ichi Tada, Ayase (JP)

(73) Assignees: TOSOH CORPORATION, Yamaguchi (JP); SAGAMI CHEMICAL RESEARCH INSTITUTE, Kanagawa (JP)

( * ) Notice: Subject to any disclaimer, the term of this patent is extended or adjusted under 35 U.S.C. 154(b) by 0 days.

(21) Appl. No.: 17/292,819

(22) PCT Filed: Nov. 8, 2019

(86) PCT No.: PCT/JP2019/043979
§ 371 (c)(1),
(2) Date: May 11, 2021

(87) PCT Pub. No.: WO2020/100765
PCT Pub. Date: May 22, 2020

(65) Prior Publication Data
US 2022/0017553 A1 Jan. 20, 2022

(30) Foreign Application Priority Data

Nov. 12, 2018 (JP) .................................. 2018-212049
Feb. 12, 2019 (JP) .................................. 2019-022221
Jul. 18, 2019 (JP) .................................. 2019-132379

(51) Int. Cl.
*C07F 15/06* (2006.01)
*C23C 16/18* (2006.01)

(52) U.S. Cl.
CPC ............ *C07F 15/065* (2013.01); *C23C 16/18* (2013.01)

(58) Field of Classification Search
None
See application file for complete search history.

(56) References Cited

U.S. PATENT DOCUMENTS

2018/0362568 A1* 12/2018 Koiso ............... H01L 23/53238
2019/0382430 A1* 12/2019 Cooper ................... C23C 16/18
(Continued)

FOREIGN PATENT DOCUMENTS

JP 2-169547 6/1990
JP 3-14534 1/1991
(Continued)

OTHER PUBLICATIONS

JP2017081857 machine translation (May 18, 2017) downloaded Sep. 29, 2022.*
(Continued)

*Primary Examiner* — Alexander R Pagano
(74) *Attorney, Agent, or Firm* — Nixon & Vanderhye, P.C.

(57) ABSTRACT

To provide a cobalt complex which is liquid at room temperature, useful for producing a cobalt-containing thin film under conditions without using an oxidizing gas.

A cobalt complex represented by the following formula (1):

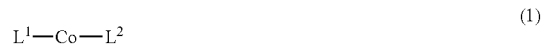

wherein $L^1$ and $L^2$ represent a unidentate amide ligand of the following formula (A), a bidentate amide ligand of the following formula (B) or a hetero atom-containing ligand of the following formula (C):

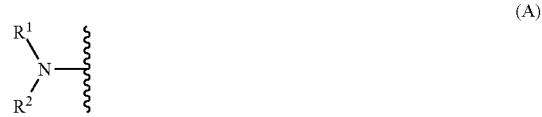

wherein $R^1$ and $R^2$ represent a $C_{1-6}$ alkyl group or a tri($C_{1-6}$ alkyl)silyl group, and the wave line represents a binding site to the cobalt atom;

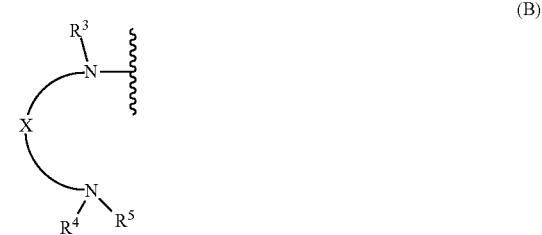

wherein $R^3$ represents a tri($C_{1-6}$ alkyl)silyl group, $R^4$ and $R^5$ represent a $C_{1-4}$ alkyl group, and X represents a $C_{1-6}$ alkylene group;

(Continued)

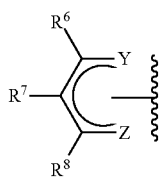

(C)

wherein $R^6$ and $R^8$ represent a $C_{1-6}$ alkyl group, $R^7$ represents a hydrogen atom or a $C_{1-4}$ alkyl group, Y represents an oxygen atom or $NR^9$, Z represents an oxygen atom or $NR^{10}$, and $R^9$ and $R^{10}$ independently represent a $C_{1-6}$ alkyl group.

18 Claims, 4 Drawing Sheets

(56) References Cited

U.S. PATENT DOCUMENTS

| | | | | |
|---|---|---|---|---|
| 2022/0025514 | A1* | 1/2022 | Winter | C23C 16/56 |
| 2022/0389570 | A1* | 12/2022 | Sakurai | C07F 15/06 |

FOREIGN PATENT DOCUMENTS

| | | | | |
|---|---|---|---|---|
| JP | 2007-153869 | | 6/2007 | |
| JP | 2009-161513 | | 7/2009 | |
| JP | 2017-81857 | | 5/2017 | |
| KR | 2010071463 | * | 6/2010 | C07K 15/0053 |
| WO | 2012/060428 | | 5/2012 | |
| WO | 2014/052316 | | 4/2014 | |

OTHER PUBLICATIONS

KR2010071463 machine translation, downloaded from Google Patents on Mar. 25, 2023.*
S. Konig et al., 53 Inorganic Chemistry, 4585-4597 (2014) (Year: 2014).*
A. Panda et al., 41 Inorganic Chemistry, 3909-3916 (2002) (Year: 2002).*
A. Pierpont et al., 49 Inorganic Chemistry, 2038-2046 (2010) (Year: 2010).*
CAS Abstract S. Konig et al., 53 Inorganic Chemistry, 4585-4597 (2014) (Year: 2014).*
International Search Report for PCT/JP2019/043979 dated Jan. 28, 2020, 7 pages.
Su et al., "Immobilization of transition metal ($Fe^2+$, $Co^2+$, $VO^2+$, or $Cu^2+$) Schiff base complexes onto garaphene oxide as efficient and recyclable catalysts for epoxidation of styrene", RSC Adv., 2014, vol. 4, pp. 9990-9996.
Wang et al., "Oxovanadium (IV), copper (II) or cobalt (II) acetylacetone complexes immobilized on amino-functionalized CMK-3 for the aerobic epoxidation of styrene", Appl. Organometal, Chem., 2015, vol. 29, pp. 698-706.
Sun et al., "Core-shell structured $F_e3O_4SiO_2$ supported cobalt (II) or copper (II) acetylacetonate complexes: magnetically recoverable nanocatalysts for aerobic epoxidation of styrene", Catalysis Science & Technology, 2014, vol. 4, pp. 1246-1252.
Database Registry, 1995 (accession date), RN 165406-56-4, Retrieved from STN international [online]; retrieved on Jan. 14, 2020 RN 165406-56-4, 2 pages.
Database Registry, 2014 (accession date), RN 1596799-36-8, Retrieved from STN international [online]; retrieved on Jan. 14, 2020 RN 1596799-36-8, 2 pages.
Database Registry, 1992 (accession date), RN 139195-99-6, Retrieved from STN international [online]; retrieved on Jan. 17, 2020, RN 139195-99-6, 2 pages.
Database Registry, 1992 (accession date), RN 139195-95-2, Retrieved from STN international [online]; retrieved on Jan. 17, 2020, RN 139195-95-2, 2 pages.
Database Registry, 2014 (accession date), RN 1581228-67-2, Retrieved from STN international [online]; retrieved on Jan. 14, 2020 RN 1581228-67-2, 2 pages.
Pierpont et al., "Computational Study of Methane C—H Activation by First-Row Late Transition Metal $L_nM=E$ (M: Fe, Co, Ni) Complexes", Inorg. Chem. 2010, vol. 49, pp. 2038-2046, Supporting Information (S1, 2, 24-31), 19 pages.
Panda et al., "Synthesis and Characterization of Three-Coordinate and Related (β-Diketiminate Derivatives of Manganese, Iron, and Cobalt", Inorg. Chem., 2002, vol. 41, No. 15, pp. 3909-3916.
Han et al., "New Heteroleptic Cobalt Precursors for Deposition of Cobalt-Based Thin Films", American Chemical Society, 2017, vol. 2, pp. 5486-5493.
Nilsen et al., "Inexpensive set-up for determination of decomposition temperature for volatile compounds", Thermochimica Acta 404, 2003, pp. 187-192.
International Preliminary Report on Patentability issued in PCT/JP2019/043979 dated May 11, 2021.
Extended European Search Report for corresponding European Application No. 19884650.3, dated Aug. 2, 2022, 8 pages.
Elena Carl et al., "Triimidosulfonates as Acute Bite-Angle Chelates: Slow Relaxation of the Magnetization in Zero Field and Hysteresis Loop of a Co II Complex", Chemistry—A Europen Journal, vol. 21, No. 28, Jun. 3, 2015, pp. 10109-10115.

* cited by examiner

COBALT COMPLEX, METHOD FOR MANUFACTURING SAME, AND METHOD FOR MANUFACTURING COBALT-CONTAINING THIN FILM

This application is the U.S. national phase of International Application No. PCT/JP2019/043979 filed Nov. 8, 2019 which designated the U.S. and claims priority to JP Patent Application No. 2018-212049 filed Nov. 12, 2018, JP Patent Application No. 2019-022221 filed Feb. 12, 2019 and JP Patent Application No. 2019-132379 filed Jul. 18, 2019, the entire contents of each of which are hereby incorporated by reference.

TECHNICAL FIELD

The present invention relates to a cobalt complex useful as a material for producing a semiconductor device, a method for producing it, and a method for producing a cobalt-containing thin film using the cobalt complex.

BACKGROUND ART

Cobalt, characterized by having high conductivity, having high work function, capable of forming a conductive silicide, being excellent in lattice matching with copper, etc., attracts attention as a material of a gate electrode, contact on a diffusion layer between source and drain portions, and a copper wiring seed layer/liner layer, of a semiconductor device such as a transistor. In the next generation semiconductor device, a highly detailed and three-dimensional design is adopted for the purpose of further improving the storage capacity and responsiveness. In order to use cobalt as a material constituting the next generation semiconductor device, it is required to establish a technique to uniformly form a cobalt-containing thin film having a thickness at a level of several nm to several tens nm on a three-dimensionally constructed substrate. As a technique to produce a metal thin film on a three-dimensionally constructed substrate, a vapor deposition method based on a chemical reaction such as atomic layer deposition (ALD) method or chemical vapor deposition (CVD) method is considered to be promising. In production of a semiconductor device, as a material to form a thin film by ALD method or CVD method, a material which has an appropriate vapor pressure and thermal stability and which can be vaporized with a stable supply amount is selected.

Non-Patent Document 1 discloses as a compound having a stricture similar to that of the cobalt complex (1) of the present invention in having a bis(trimethylsilyl)amide ligand or a diketonate ligand, (1-dimethylamino-2-methyl-2-propoxy)[bis(trimethylsilyl)amino] cobalt (K1) and (1-dimethylamino-2-methyl-2-propoxy)(2,2,6,6-tetramethyl-3,5-heptanedionate) cobalt (K2), but they are different from the cobalt complex of the present invention in having an alkoxy ligand.

Non Patent Document 2 discloses, as a compound having a structure similar to the cobalt complex (1) of the present invention in having a diketonate ligand, bis(2,2,6,6-tetramethyl-3,5-heptanedionate) cobalt (K3), but it is different from the cobalt complex of the present invention in having two 2,2,6,6-tetramethyl-3,5-heptanedionate ligands.

Patent Document 1 discloses, as a compound having a structure similar to the cobalt complex (1) of the present invention in having a bis(trimethylsilyl)amide ligand, bis[bis(trimethylsilyl)amide] cobalt (K4), but it is different from the cobalt complex of the present invention in having two bis(trimethylsilyl)amide ligands.

Patent Document 2 discloses, as a compound having a structure similar to the cobalt complex (1) of the present invention in having an aminoalkylamide ligand, bis{[2-(dimethylamino)ethyl](trimethylsilyl)amino} cobalt (K5), but it is different from the cobalt complex of the present invention in having two aminoalkylamide ligands.

The melting points of the compounds (K1), (K2), (K3), (K4) and (K5) are so high as 90° C., 131° C., 118° C., 64° C. and 92 to 93° C., respectively. When these compounds are used as a material for the CVD method or the ALD method, it is required to keep the material at high temperature of at least the melting point for the purpose of keeping the vaporization rate to be sufficient and constant. However, these compounds may be decomposed by heating for a long time. Further, use of a solid material in the form of solid as it is as the material for the CVD method or the ALD method, may cause problems in supply of the material gas such as insufficient vaporization amount and changes with time of the vaporization rate, and problems in transport of the material such as in-line clogging by precipitation of solid, and further, may cause contamination of the prepared film surface by particles. Further, also in a process of e.g. a solution CVD method of using a solution having a solid precursor dissolved in an organic solvent, the solid may be precipitated due to a temperature change in the vaporization apparatus or a concentration change by partial volatilization of the solvent, and it is difficult to completely avoid problems as described above.

As the contact on the gate electrode or the diffusion layer between source and drain portions of the next generation semiconductor device, $CoSi_2$ obtained by forming a cobalt film, followed by silicification has been studied. On the other hand, in a case where cobalt is used as a copper wiring seed layer/liner layer, for the undercoat layer, use of titanium nitride or tantalum nitride as a barrier layer is expected. Further in recent years, it is studied to use cobalt as a cap layer on the copper wiring. In production of a cobalt-containing thin film, if silicon, the barrier layer or the copper wiring is oxidized, conduction failure to the transition resulting from an increase of the resistance may occur.

Therefore, a material which is liquid at room temperature and which makes it possible to produce a cobalt-containing thin film under conditions without using an oxidizing gas such as oxygen or ozone as a reaction gas has been desired.

PRIOR ART DOCUMENTS

Patent Documents

Patent Document 1: WO2014/052316
Patent Document 2: JP-A-2017-81857

Non-patent Documents

Non-Patent Document 1: ACS Omega, vol. 2, p. 5486 (2017)
Non-Patent Document 2: Thermochimica Acta, Vol. 404, p. 187 (2003)

DISCLOSURE OF INVENTION

Technical Problem

The object of the present invention is to provide a cobalt complex which is liquid at room temperature and which makes it possible to produce a cobalt-containing thin film under conditions without using an oxidizing gas.

Solution to Problem

The present inventors have conducted extensive studies to achieve the above object and as a result, found that a novel cobalt complex represented by the following formula (1) is useful as a material which is liquid at room temperature to produce a cobalt-containing thin film under conditions without using an oxidizing gas, particularly under conditions using a reducing gas, and accomplished the present invention.

That is, the present invention relates to a cobalt complex represented by the following formula (1):

(1)

wherein $L^1$ and $L^2$ which are different from each other represent a unidentate amide ligand represented by the following formula (A), a bidentate amide ligand represented by the following formula (B) or a hetero atom-containing ligand represented by the following formula (C):

(A)

wherein $R^1$ and $R^2$ independently represent a $C_{1-6}$ alkyl group or a tri($C_{1-6}$ alkyl)silyl group, and the wave line represents a binding site to the cobalt atom;

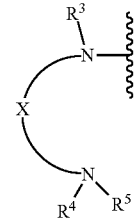
(B)

wherein $R^3$ represents a tri($C_{1-6}$ alkyl)silyl group, $R^4$ and $R^5$ independently represent a $C_{1-4}$ alkyl group, and X represents a $C_{1-6}$ alkylene group;

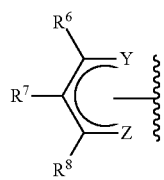
(C)

wherein $R^6$ and $R^9$ independently represent a $C_{1-6}$ alkyl group, $R^7$ represents a hydrogen atom or a $C_{1-4}$ alkyl group, Y represents an oxygen atom or $NR^9$, Z represents an oxygen atom or $NR^{10}$, and $R^9$ and $R^{10}$ independently represent a $C_{1-6}$ alkyl group.

More specifically, the present invention relates to a cobalt complex represented by the following formula (1AB), a cobalt complex represented by the following formula (1AC) and a cobalt complex represented by the following formula (1BC):

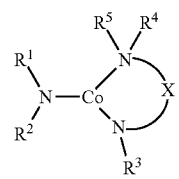
(1AB)

wherein $R^1$ and $R^2$ are as defined for $R^1$ and $R^2$ in the above formula (A), and $R^3$, $R^4$, $R^5$ and X are as defined for $R^3$, $R^4$, $R^5$ and X in the above formula (B);

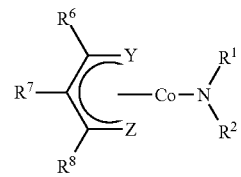
(1AC)

wherein $R^1$ and $R^2$ are as defined for $R^1$ and $R^2$ in the above formula (A), and $R^6$, $R^7$, $R^8$, Y and Z are as defined for $R^6$, $R^7$, $R^8$, Y and Z in the above formula (C);

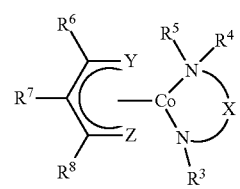
(1BC)

wherein $R^3$, $R^4$, $R^5$ and X are as defined for $R^3$, $R^4$, $R^5$ and X in the above formula (B), and $R^6$, $R^7$, $R^8$, Y and Z are as defined for $R^6$, $R^7$, $R^8$, Y and Z in the above formula (C).

The present invention further relates to a method for producing a cobalt complex represented by the formula (1AB), which comprises reacting a bisamide complex represented by the following formula (2) and an aminoalkylamine represented by the following formula (3):

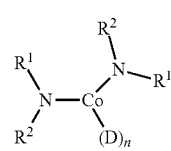
(2)

wherein $R^1$ and $R^2$ independently represent a $C_{1-6}$ alkyl group or a tri($C_{1-6}$ alkyl)silyl group, D represents a neutral ligand, and n represents 0 or 1;

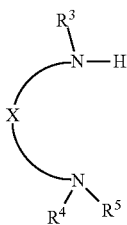

(3)

wherein $R^3$ represents a tri($C_{1-6}$ alkyl)silyl group, $R^4$ and $R^5$ independently represent a $C_{1-6}$ alkyl group, and X represents a $C_{1-6}$ alkylene group.

The present invention further relates to a method for producing a cobalt complex represented by the formula (1AC), which comprises reacting a bisamide complex represented by the above formula (2) and a hetero atom-containing compound represented by the following formula (4):

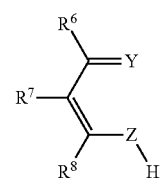

(4)

wherein $R^6$ and $R^8$ independently represent a $C_{1-6}$ alkyl group, $R^7$ represents a hydrogen atom or a $C_{1-4}$ alkyl group, Y represents an oxygen atom or $NR^9$, Z represents an oxygen atom or $NR^{10}$, and $R^9$ and $R^{10}$ independently represent a $C_{1-6}$ alkyl group.

The present invention further relates to a method for producing a cobalt complex represented by the formula (1 BC), which comprises reacting the cobalt complex (1AB) and the hetero atom-containing compound (4).

The present invention further relates to a method for producing a cobalt-containing thin film, which comprises using the cobalt complex represented by the formula (1) for a vapor deposition method based on a chemical reaction.

Advantageous Effects of Invention

The cobalt complex (I) of the present invention is liquid at room temperature, and by using it as a material, it is possible to produce a cobalt-containing thin film under conditions without using an oxidizing gas.

DESCRIPTION OF EMBODIMENTS

Figure 1:
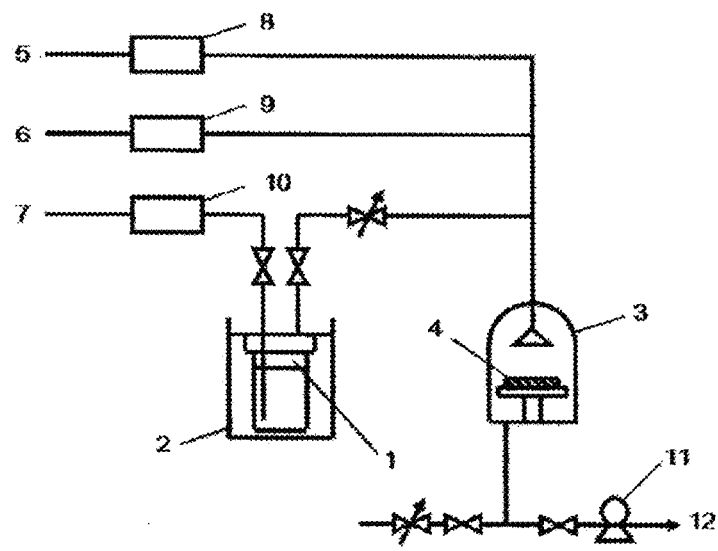
FIG. 1 is a drawing schematically illustrating a CVD apparatus used in Examples 8 to 11, 13 to 15 and 19 to 25 and Comparative Example 3.

Now, the present invention will be described in detail.

In this specification, "complex represented by the formula (1)" may sometimes be referred to as "complex (1)". The same applies to other complexes and compounds.

First, definitions of $L^1$ and $L^2$ in the formula (1) will be described. $L^1$ and $L^2$ in the formula (1) are any one of a unidentate amide ligand (A), a bidentate amide ligand (B) and a hetero atom-containing ligand (C), and $L^1$ and $L^2$ are not the same.

Now, definitions of $R^1$ and $R^2$ in the formula (A) will be described. The $C_{1-6}$ alkyl group represented by $R^1$ and $R^2$ may be any of linear, branched and cyclic, and may, for example, be specifically a methyl group, an ethyl group, a propyl group, an isopropyl group, a cyclopropyl group, a butyl group, an isobutyl group, a sec-butyl group, a tert-butyl group, a cyclobutyl group, a pentyl group, a 1-ethylpropyl group, a 1-methylbutyl group, a 2-methylbutyl group, an isopentyl group, a neopentyl group, a tert-pentyl group, a cyclopentyl group, a cyclobutylmethyl group, a hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethyl butyl group, a 2,3-dimethylbutyl group, a 3,3-dimethylbutyl group, a cyclohexyl group, a cyclopentylmethyl group, a 1-cyclobutylethyl group or a 2-cyclobutylethyl group. The $C_{1-6}$ alkyl group in the tri($C_{1-6}$ alkyl)silyl group represented by $R^1$ and $R^2$ may be any of linear, branched and cyclic, and the tri($C_{1-6}$ alkyl)silyl group may, for example, be specifically a trimethylsilyl group, an ethyldimethylsilyl group, a diethyl(methyl)silyl group, a dimethyl(propyl)silyl group, an isopropyldimethylsilyl group, a triethylsilyl group, a butyldimethylsilyl group, an isobutyldimethylsilyl group, a sec-butyldimethylsilyl group, a tert-butyldimethylsilyl group, a cyclobutyldimethylsilyl group, a diethyl(propyl)silyl group, a diethyl(isopropyl)silyl group, a tripropylsilyl group, a triisopropylsilyl group, a pentyldimethylsilyl group, a pentyldiethylsilyl group, a tripentylsilyl group, a hexyldimethylsilyl group, a cyclohexyldimethylsilyl group, a hexyldiethylsilyl group, a cyclohexyldiethylsilyl group or a trihexylsilyl group. $R^1$ and $R^2$ are preferably a $C_{1-4}$ alkyl group or a tri($C_{1-6}$ alkyl)silyl group, more preferably a tri($C_{1-4}$ alkyl)silyl group, further preferably a trimethylsilyl group, an ethyldimethylsilyl group, a diethyl(methyl)silyl group, a triethylsilyl group or a tert-butyldimethylsilyl group, especially preferably a trimethylsilyl group, whereby the cobalt complex (1) will have an appropriate vapor pressure and thermal stability as the CVD material and the ALD material.

Now, definition of $R^3$ in the formula (B) will be described. The $C_{1-6}$ alkyl group in the tri($C_{1-6}$ alkyl)silyl group represented by $R^3$ may be any of linear, branched and cyclic, and the tri($C_{1-6}$ alkyl)silyl group may for example, be specifically a trimethylsilyl group, an ethyldimethylsilyl group, a diethyl(methyl)silyl group, a propyldimethylsilyl group, an isopropyldimethylsilyl group, a triethylsilyl group, a butyldimethylsilyl group, an isobutyldimethylsilyl group, a sec-butyldimethylsilyl group, a tert-butyldimethylsilyl group, a cyclobutyldimethylsilyl group, a diethyl(propyl)

silyl group, a diethyl(isopropyl)silyl group, a tripropylsilyl group, a triisopropylsilyl group, a pentyldimethylsilyl group, a pentyldiethylsilyl group, a tripentylsilyl group, a hexyldimethylsilyl group, a cyclohexyldimethylsilyl group, a hexyldiethylsilyl group, a cyclohexyldiethylsilyl group or a trihexylsilyl group. The tri($C_{1-6}$ alkyl)silyl group represented by $R^3$ is preferably a tri($C_{1-4}$ alkyl)silyl group, more preferably a trimethylsilyl group, an ethyldimethylsilyl group, a diethyl(methyl)silyl group, a triethylsilyl group or a tert-butyldimethylsilyl group, especially preferably a trimethylsilyl group, whereby the cobalt complex (1) will have an appropriate vapor pressure and thermal stability as the CVD material and the ALD material.

Now, definitions of $R^4$ and $R^5$ in the formula (B) will be described. The $C_{1-4}$ alkyl group represented by $R^4$ and $R^5$ may be any of linear, branched and cyclic, and may, for example, be specifically a methyl group, an ethyl group, a propyl group, an isopropyl group, a cyclopropyl group, a butyl group, an isobutyl group, a sec-butyl group, a tert-butyl group or a cyclobutyl group. $R^4$ and $R^5$ are preferably a methyl group or an ethyl group, more preferably a methyl group, whereby the cobalt complex (1) will have an appropriate vapor pressure and thermal stability as the CVD material and the ALD material.

Now, definition of X in the formula (B) will be described.

The $C_{1-6}$ alkylene group represented by X may be any of linear and branched, and may, for example, be a methylene group, a dimethylmethylene group, a 1,2-ethylene group, a 1-methyl-1,2-ethylene group, a 1,1-dimethyl-1,2-ethylene group, a 1,2-dimethyl-1,2-ethylene group, a trimethylene group, or a tetramethylene group. X is preferably a $C_{1-4}$ alkylene group, more preferably a 1,2-ethylene group or a 1,1-dimethyl-1,2-ethylene group, especially preferably a 1,1-dimethyl-1,2-ethylene group, whereby the cobalt complex (1) will have an appropriate vapor pressure and thermal stability as the CVD material and the ALD material.

Now, definitions of $R^6$, $R^7$ and $R^8$ in the formula (C) will be described.

The $C_{1-6}$ alkyl group represented by $R^6$ and $R^8$ may be any of linear, branched and cyclic, and may, for example, be specifically a methyl group, an ethyl group, a propyl group, an isopropyl group, a cyclopropyl group, a butyl group, an isobutyl group, a sec-butyl group, a tert-butyl group, a cyclobutyl group, a pentyl group, a 1-ethylpropyl group, a 1-methylbutyl group, a 2-methylbutyl group, an isopentyl group, a neopentyl group, a tert-pentyl group, a cyclopentyl group, a cyclobutylmethyl group, a hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a cyclohexyl group, a cyclopentylmethyl group, a 1-cyclobutylethyl group or a 2-cyclobutylethyl group. $R^6$ and $R^8$ are preferably a $C_{1-4}$ alkyl group, whereby the cobalt complex (1) will have an appropriate vapor pressure and thermal stability as the CVD material and the ALD material, and particularly in a case where the cobalt complex (1) is the cobalt complex (1AC), they are more preferably a methyl group, and in a case where the cobalt complex (1) is the cobalt complex (1 BC), they are more preferably a tert-butyl group.

The $C_{1-4}$ alkyl group represented by $R^7$ may be any of linear, branched and cyclic, and may, for example, be specifically a methyl group, an ethyl group, a propyl group, an isopropyl group, a cyclopropyl group, a butyl group, an isobutyl group, a sec-butyl group, a tert-butyl group or a cyclobutyl group. $R^7$ is preferably a hydrogen atom, whereby the cobalt complex (1) will have an appropriate vapor pressure and thermal stability as the CVD material and the ALD material.

The $C_{1-6}$ alkyl group represented by $R^9$ and $R^{10}$ may be any of linear, branched and cyclic, and may, for example, be specifically a methyl group, an ethyl group, a propyl group, an isopropyl group, a cyclopropyl group, a butyl group, an isobutyl group, a sec-butyl group, a tert-butyl group, a cyclobutyl group, a pentyl group, a 1-ethylpropyl group, a 1-methylbutyl group, a 2-methylbutyl group, an isopentyl group, a neopentyl group, a tert-pentyl group, a cyclopentyl group, a cyclobutylmethyl group, a hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a cyclohexyl group, a cyclopentylmethyl group, a 1-cyclobutylethyl group or a 2-cyclobutylethyl group. $R^9$ and $R^{10}$ are preferably a $C_{1-4}$ alkyl group, more preferably a propyl group, an isopropyl group or a tert-butyl group, whereby the cobalt complex (1) will have an appropriate vapor pressure and thermal stability as the CVD material and the ALD material.

The cobalt complex (1) is preferably the cobalt complex represented by the formula (1AB) having a unidentate amide ligand represented by the formula (A) and a bidentate amide ligand represented by the formula (B), the cobalt complex represented by the formula (1AC) having a unidentate amide ligand represented by the formula (A) and a hetero atom-containing ligand represented by the formula (C), or the cobalt complexes (1AC) having a bidentate amide ligand represented by the formula (B) and a hetero atom-containing ligand represented by the formula (C).

The hetero atom-containing ligands represented by the formula (C) in the cobalt complexes (1AC) and (1 BC) respectively have the following resonance structures (1AC-R1) and (1AC-R2), and (1BC-R1) and (1BC-R2), and in this specification, for simplification, they are respectively represented by (1AC) and (1 BC).

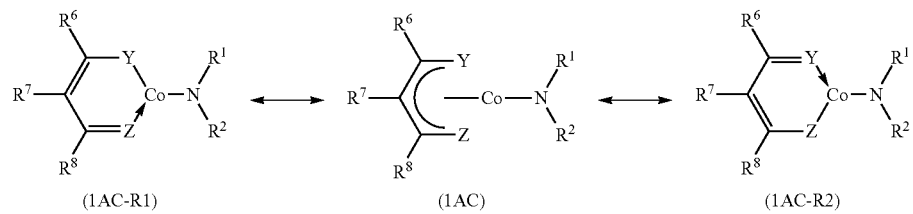

(1AC-R1)     (1AC)     (1AC-R2)

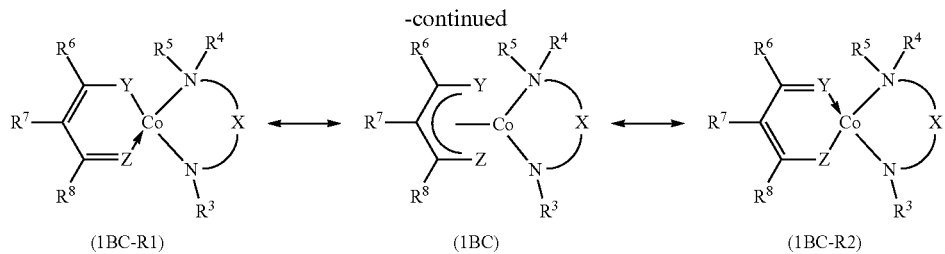
(1BC-R1)     (1BC)     (1BC-R2)
In the formulae, $R^6$, $R^7$, $R^8$, Y and Z are as defined above.
Among the cobalt complexes (1), as specific examples of the cobalt complex (1AB), the following (1AB-1) to (1AB-66) may, for example, be mentioned.
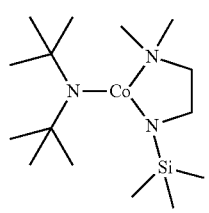
(1AB-1)
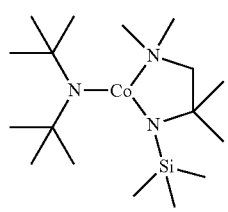
(1AB-2)
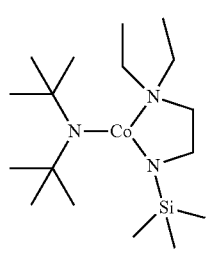
(1AB-3)
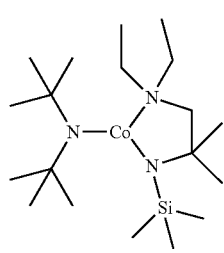
(1AB-4)
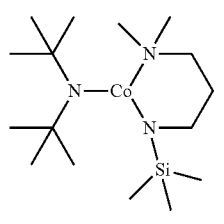
(1AB-5)
-continued
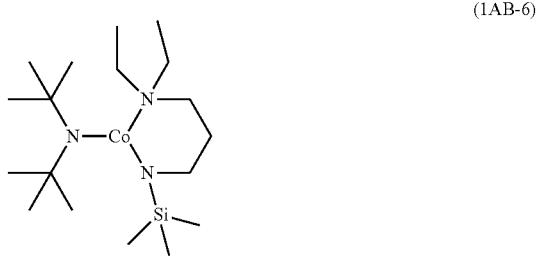
(1AB-6)
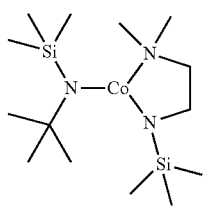
(1AB-7)
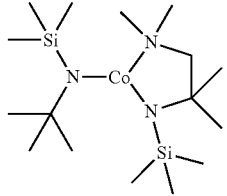
(1AB-8)
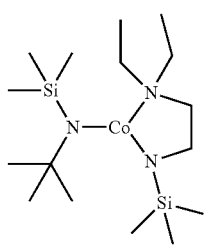
(1AB-9)
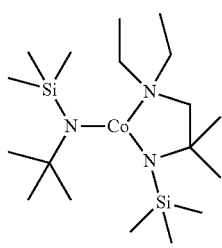
(1AB-10)

(1AB-11)
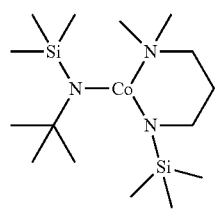
(1AB-12)
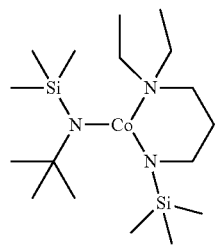
(1AB-13)
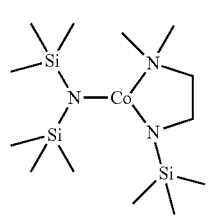
(1AB-14)
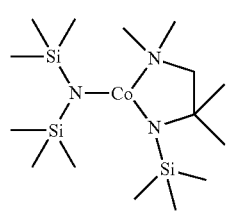
(1AB-15)
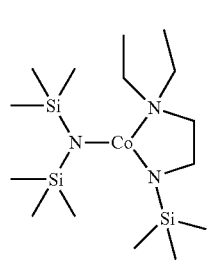
(1AB-16)
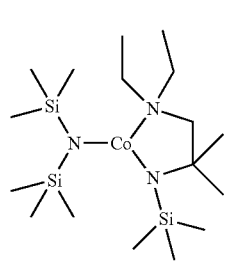
(1AB-17)
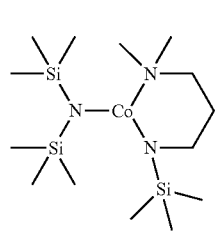
(1AB-18)
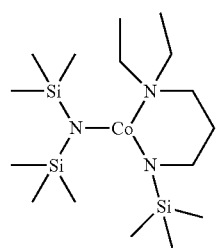
(1AB-19)
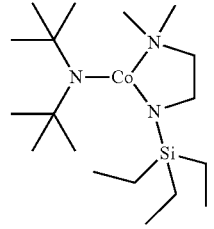
(1AB-20)
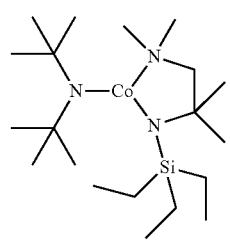
(1AB-21)
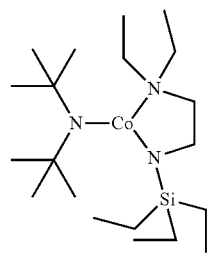
(1AB-22)
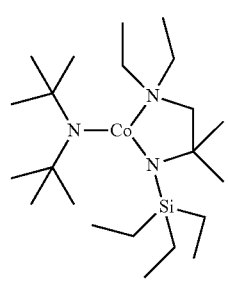
(1AB-23)
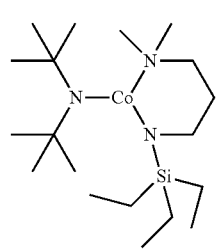

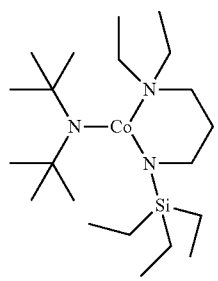
(1AB-24)
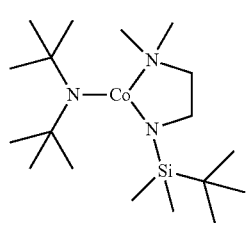
(1AB-25)
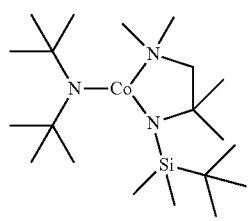
(1AB-26)
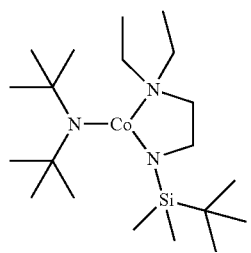
(1AB-27)
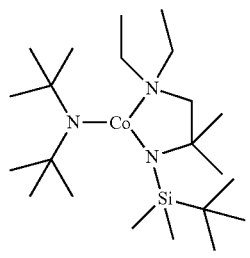
(1AB-28)
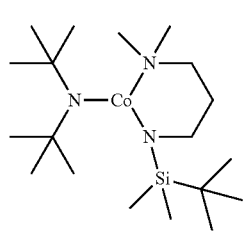
(1AB-29)
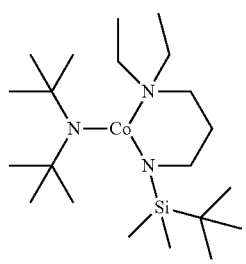
(1AB-30)
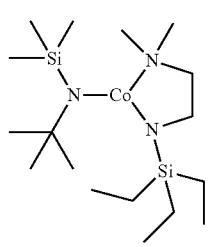
(1AB-31)
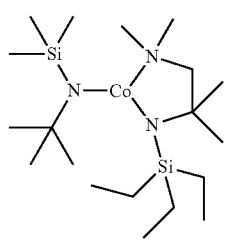
(1AB-32)
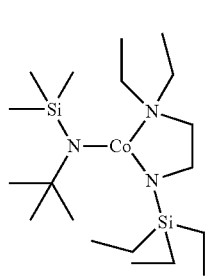
(1AB-33)
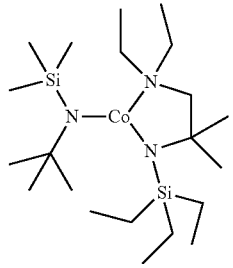
(1AB-34)
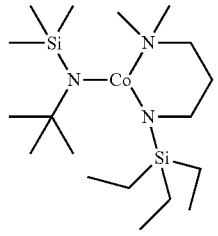
(1AB-35)

(1AB-36)
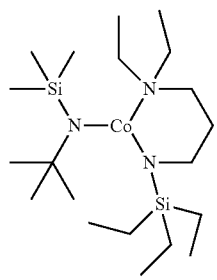
(1AB-42)
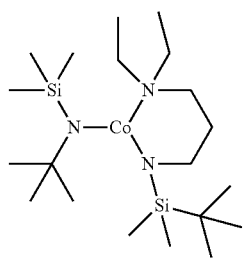
(1AB-37)
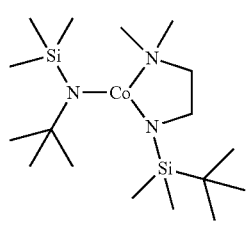
(1AB-43)
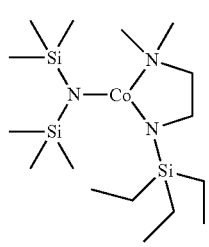
(1AB-38)
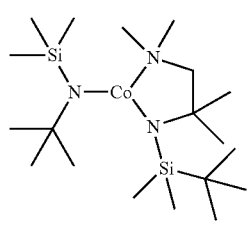
(1AB-44)
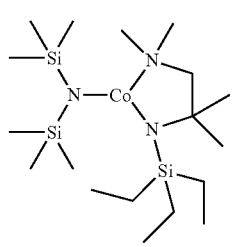
(1AB-39)
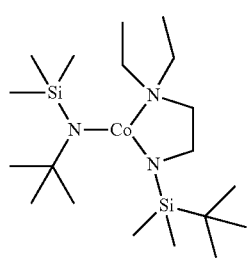
(1AB-45)
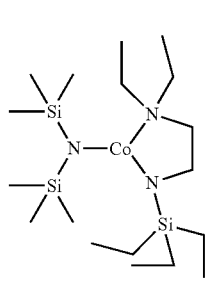
(1AB-40)
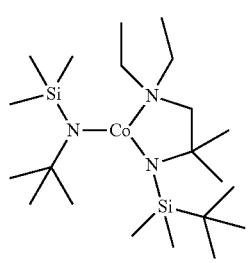
(1AB-46)
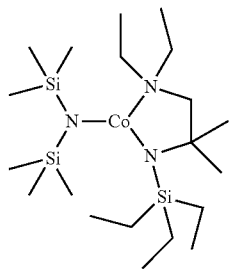
(1AB-41)
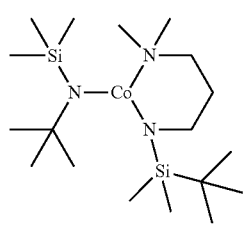
(1AB-47)
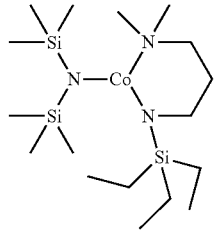

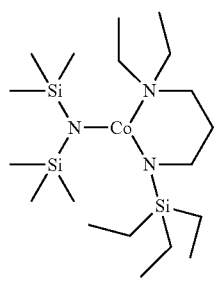
(1AB-48)
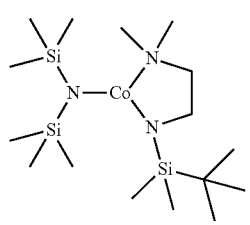
(1AB-49)
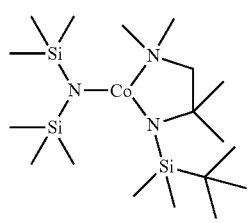
(1AB-50)
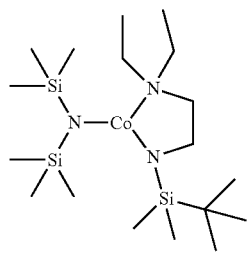
(1AB-51)
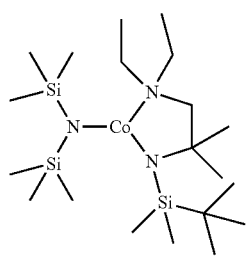
(1AB-52)
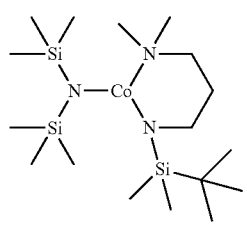
(1AB-53)
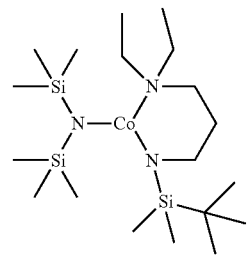
(1AB-54)
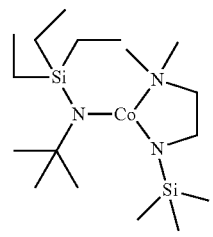
(1AB-55)
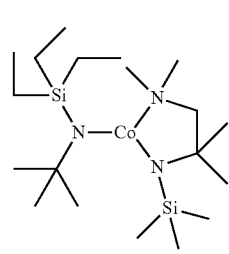
(1AB-56)
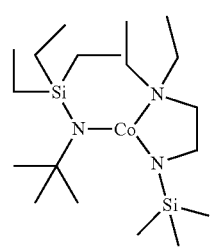
(1AB-57)
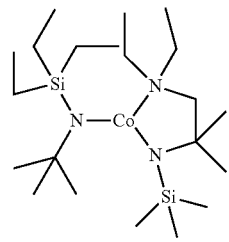
(1AB-58)
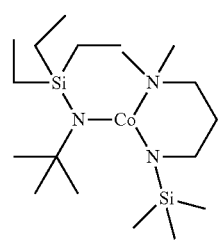
(1AB-59)

(1AB-60) 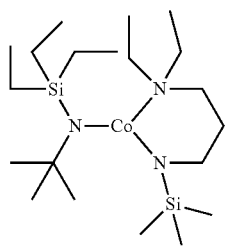

(1AB-61) 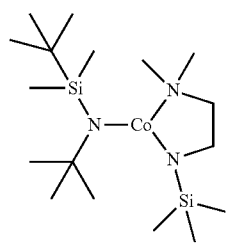

(1AB-62) 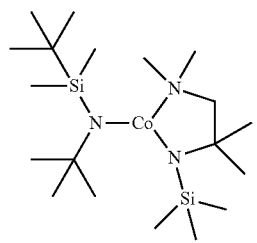

(1AB-63) 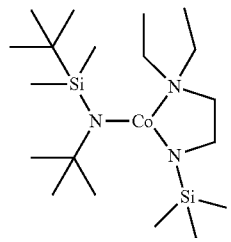

(1AB-64) 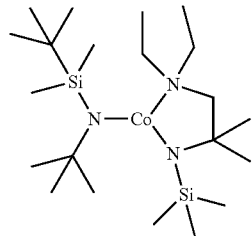

(1AB-65) 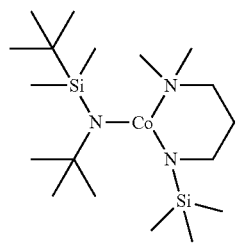

(1AB-66) 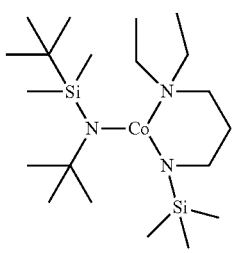

Among the above, (1AB-7), (1AB-8), (1AB-9), (1AB-10), (1AB-13), (1AB-14), (1AB-15), (1AB-16) and (1AB-50) are preferred, (1AB-8), (1AB-13), (1AB-14), (1AB-16) and (1AB-50) are more preferred, and (1AB-14) is further preferred, which have an appropriate vapor pressure and thermal stability as the CVD material and the ALD material.

Among the cobalt complexes (1), as specific examples of the cobalt complex (1AC), the following (1AC-1) to (1AC-36) may, for example, be mentioned.

(1AC-1) 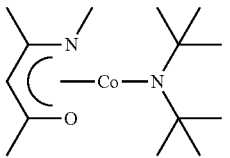

(1AC-2) 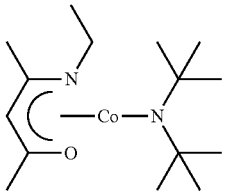

(1AC-3) 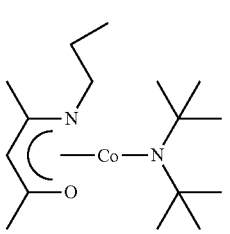

(1AC-4) 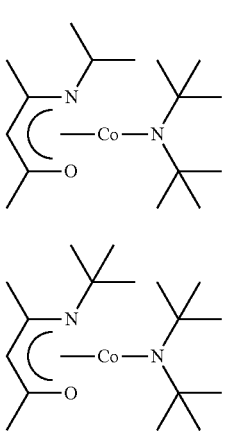

(1AC-5)

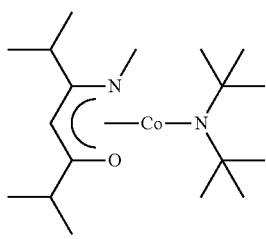 (1AC-6)
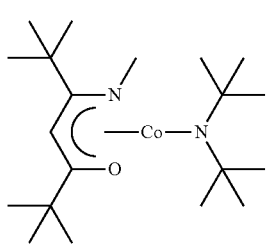 (1AC-7)
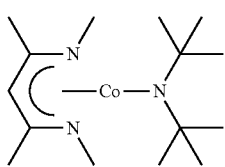 (1AC-8)
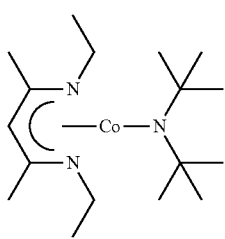 (1AC-9)
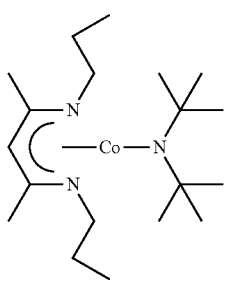 (1AC-10)
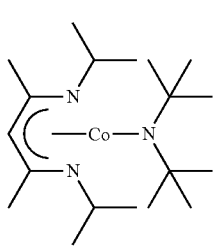 (1AC-11)
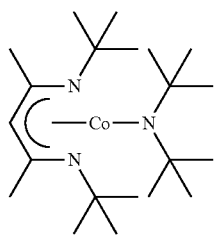 (1AC-12)
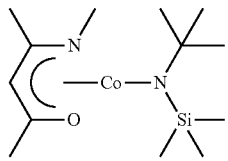 (1AC-13)
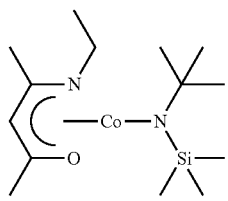 (1AC-14)
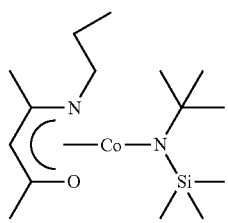 (1AC-15)
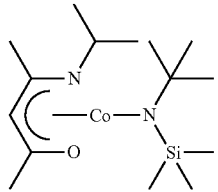 (1AC-16)
(1AC-17)
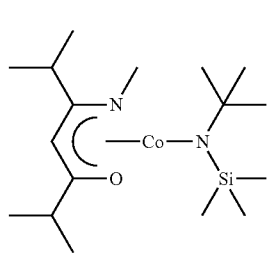 (1AC-18)

(1AC-19)
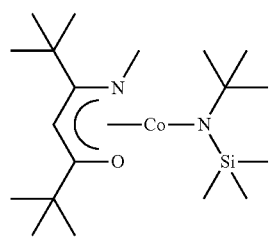
(1AC-20)
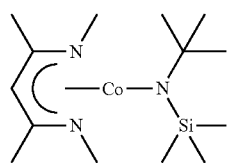
(1AC-21)
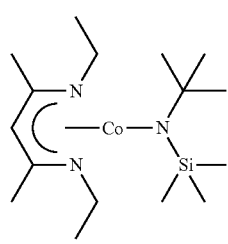
(1AC-22)
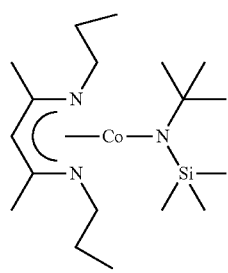
(1AC-23)
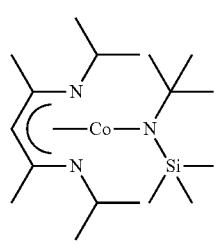
(1AC-24)
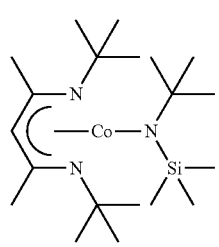
(1AC-25)
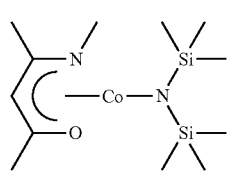
(1AC-26)
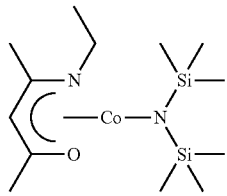
(1AC-27)
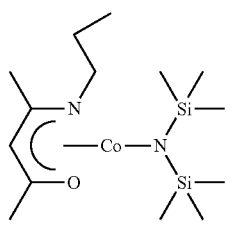
(1AC-28)
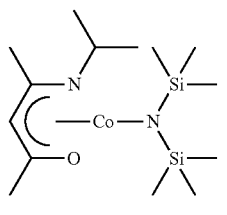
(1AC-29)
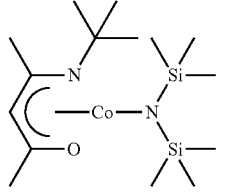
(1AC-30)
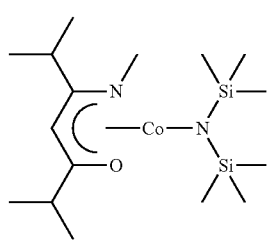
(1AC-31)
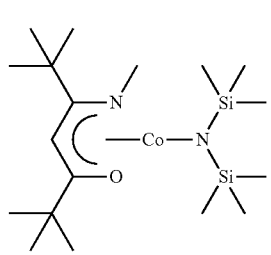
(1AC-32)

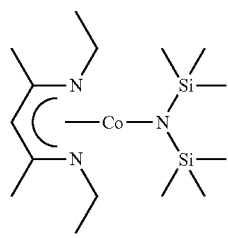
(1AC-33)
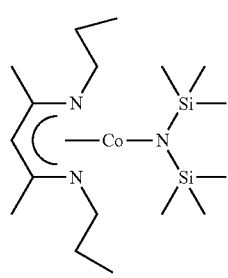
(1AC-34)
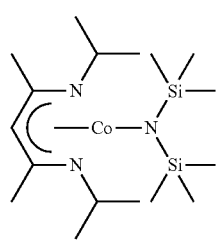
(1AC-35)
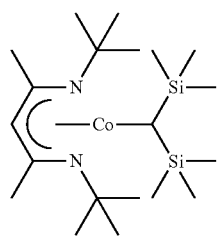
(1AC-36)
(1AC-25) to (1AC-29) and (1AC-32) to (1AC-36) are preferred, (1AC-32) to (1AC-36) are more preferred, and (1AC-34) is further preferred, which have an appropriate vapor pressure and thermal stability as the CVD material and the ALD material.
Among the cobalt complexes (1), as specific examples of the cobalt complex (1BC), the following (1 BC-1) to (1 BC-120) may, for example, be mentioned.
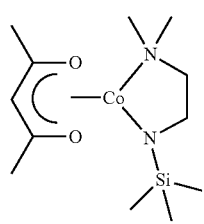
(1BC-1)
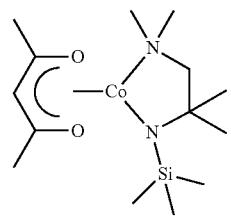
(1BC-2)
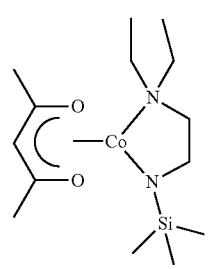
(1BC-3)
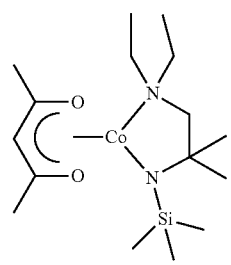
(1BC-4)
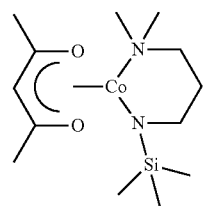
(1BC-5)
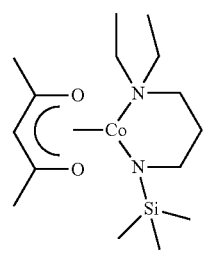
(1BC-6)
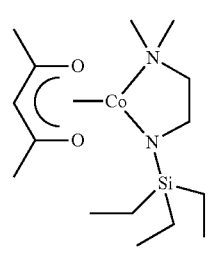
(1BC-7)

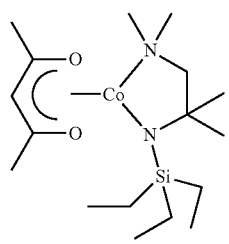
(1BC-8)
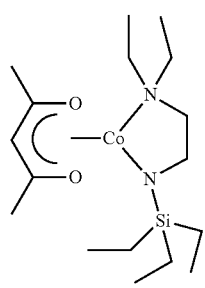
(1BC-9)
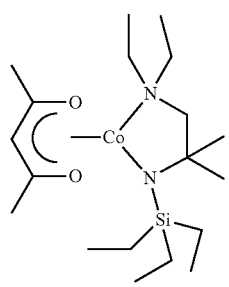
(1BC-10)
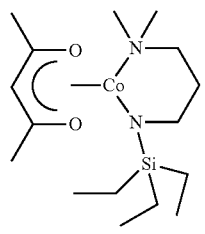
(1BC-11)
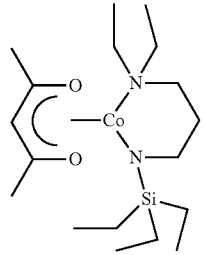
(1BC-12)
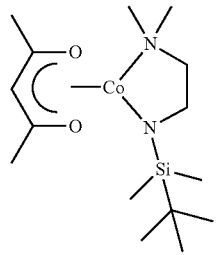
(1BC-13)
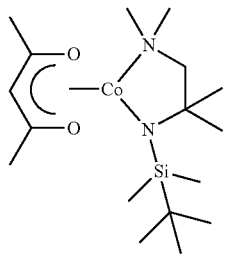
(1BC-14)
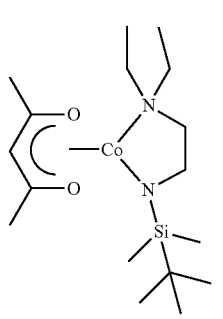
(1BC-15)
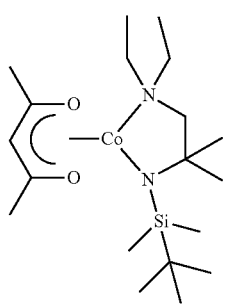
(1BC-16)
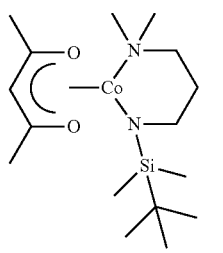
(1BC-17)
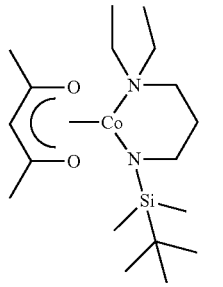
(1BC-18)

(1BC-19)
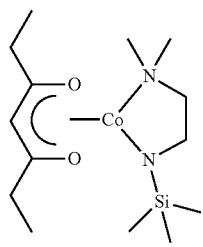
(1BC-20)
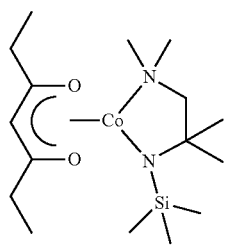
(1BC-21)
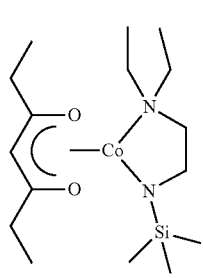
(1BC-22)
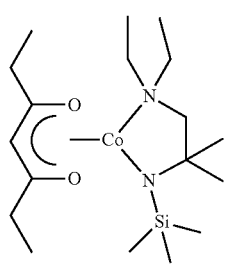
(1BC-23)
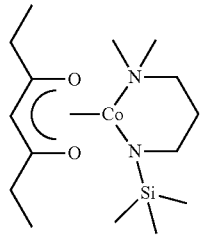
(1BC-24)
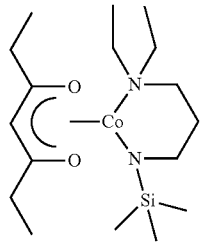
(1BC-25)
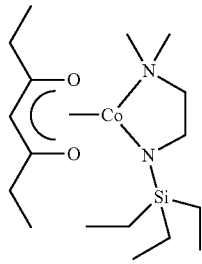
(1BC-26)
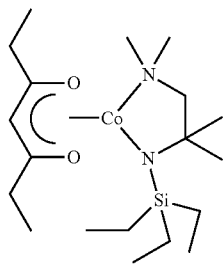
(1BC-27)
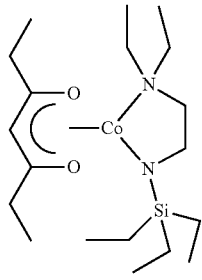
(1BC-28)
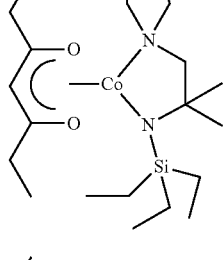
(1BC-29)
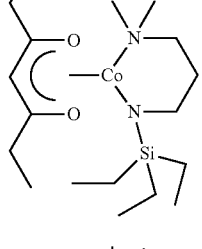
(1BC-30)
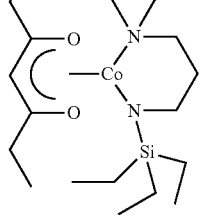

(1BC-31)
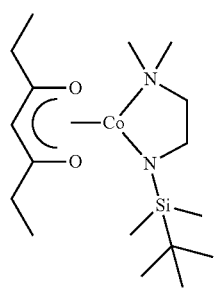
(1BC-32)
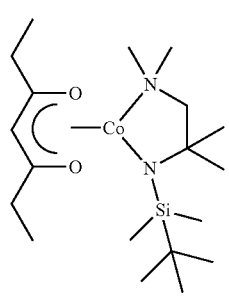
(1BC-33)
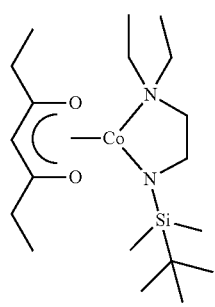
(1BC-34)
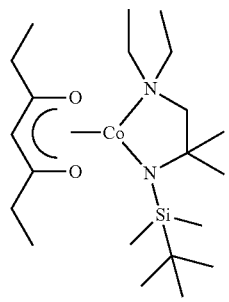
(1BC-35)
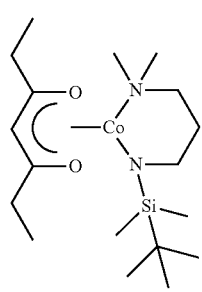
(1BC-36)
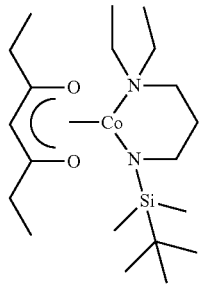
(1BC-37)
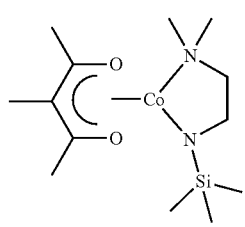
(1BC-38)
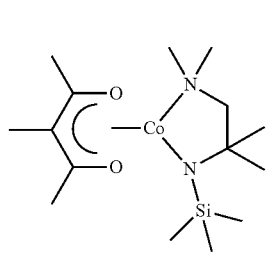
(1BC-39)
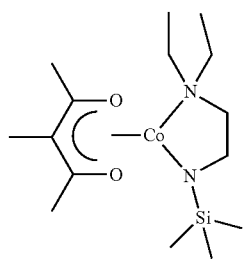
(1BC-40)
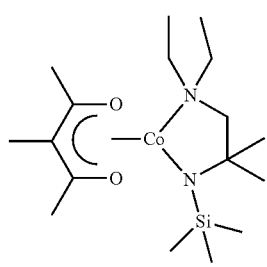
(1BC-41)
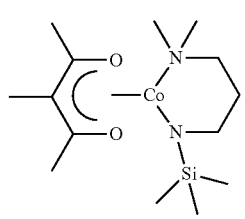

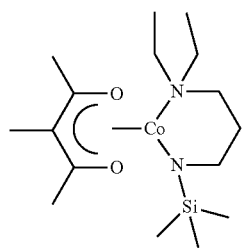
(1BC-42)
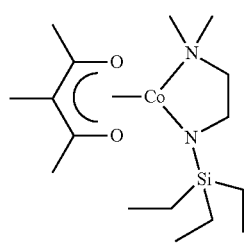
(1BC-43)
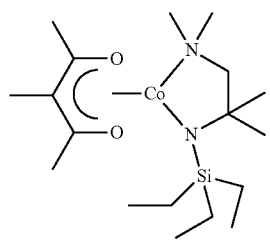
(1BC-44)
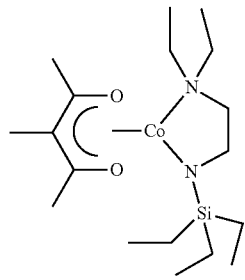
(1BC-45)
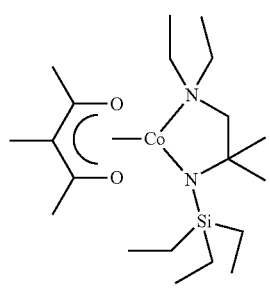
(1BC-46)
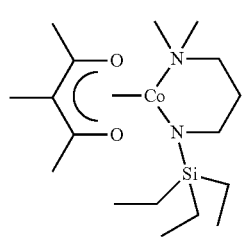
(1BC-47)
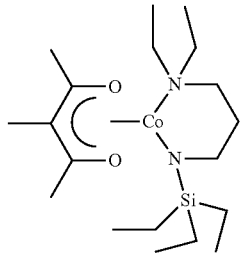
(1BC-48)
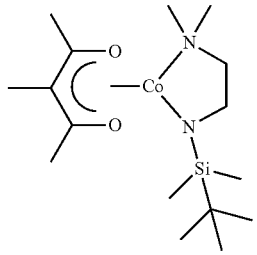
(1BC-49)
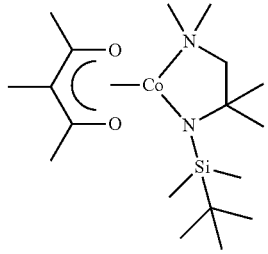
(1BC-50)
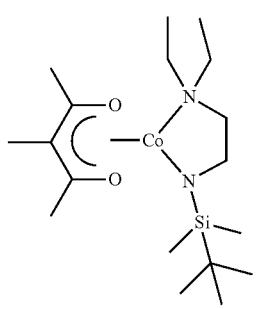
(1BC-51)
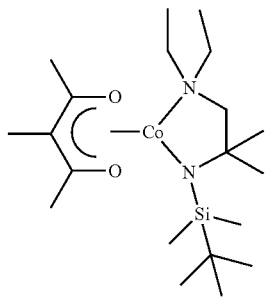
(1BC-52)
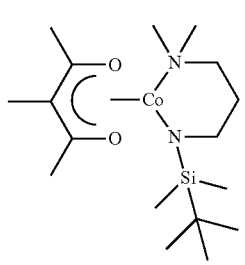
(1BC-53)

-continued
(1BC-54)
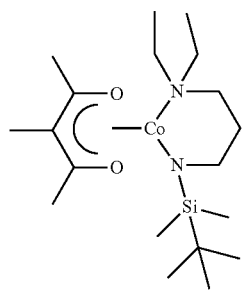
(1BC-55)
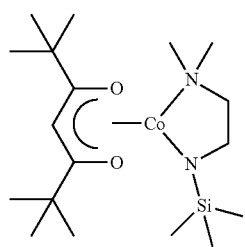
(1BC-56)
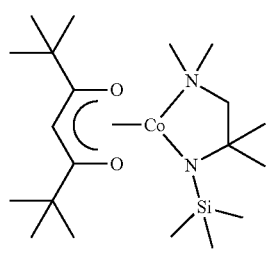
(1BC-57)
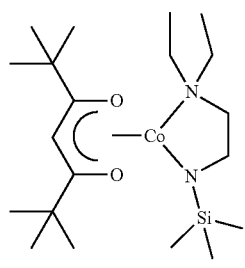
(1BC-58)
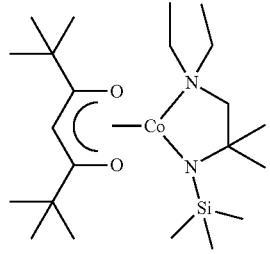
(1BC-59)
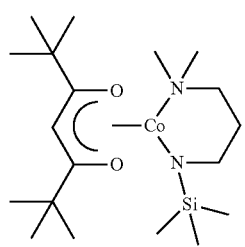
-continued
(1BC-60)
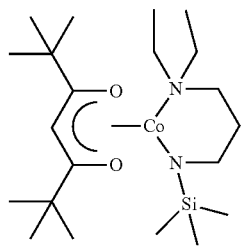
(1BC-61)
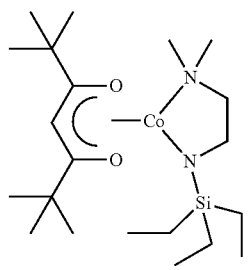
(1BC-62)
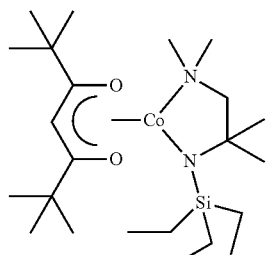
(1BC-63)
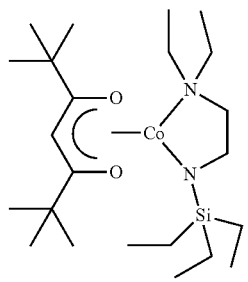
(1BC-64)
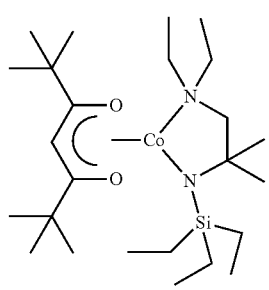
(1BC-65)
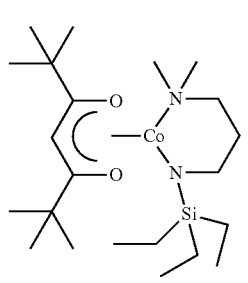

(1BC-66)
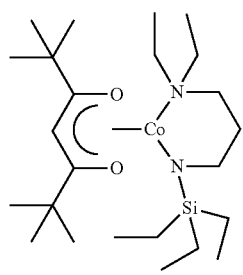
(1BC-67)
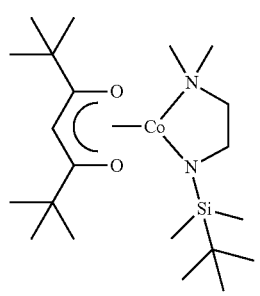
(1BC-68)
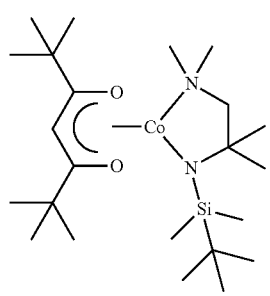
(1BC-69)
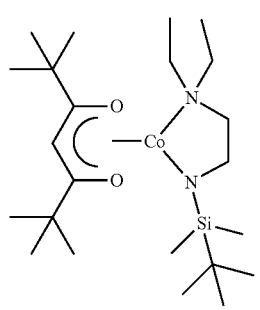
(1BC-70)
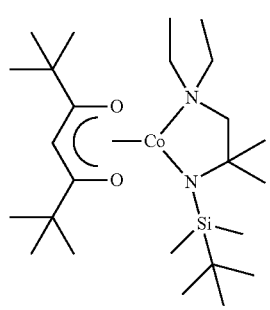
(1BC-71)
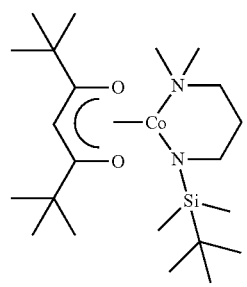
(1BC-72)
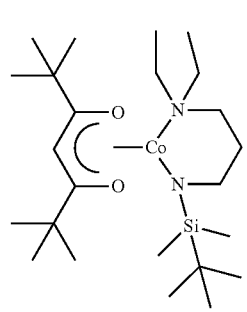
(1BC-73)
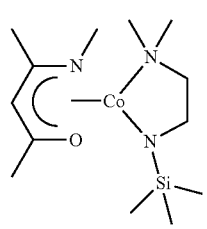
(1BC-74)
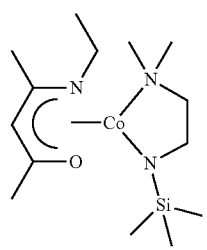
(1BC-75)
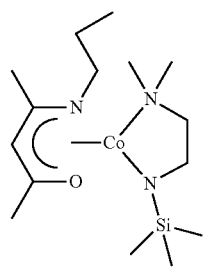
(1BC-76)
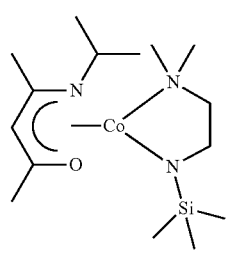

-continued
(1BC-77)
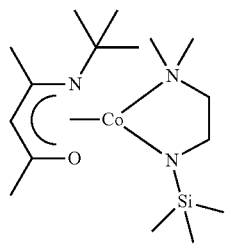
(1BC-78)
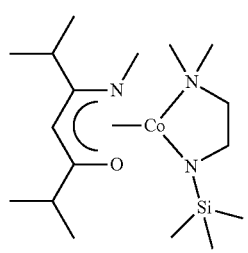
(1BC-79)
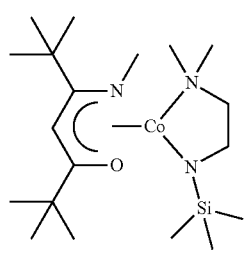
(1BC-80)
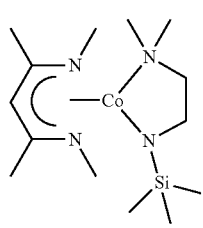
(1BC-81)
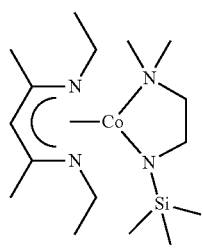
(1BC-82)
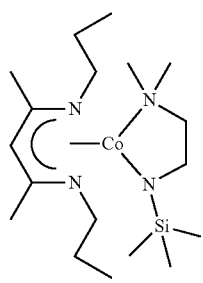
-continued
(1BC-83)
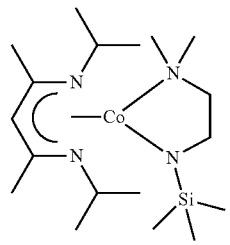
(1BC-84)
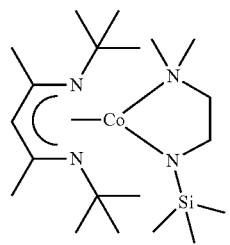
(1BC-85)
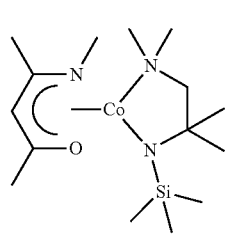
(1BC-86)
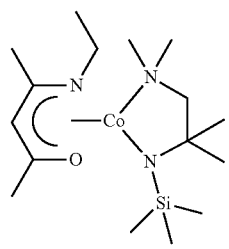
(1BC-87)
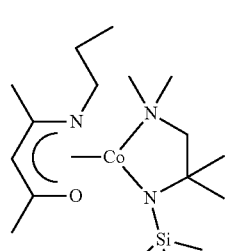
(1BC-88)
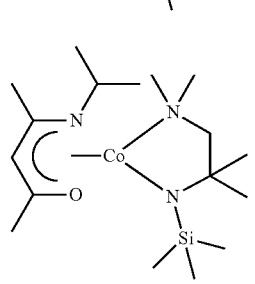

(1BC-89)
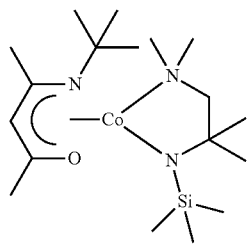
(1BC-90)
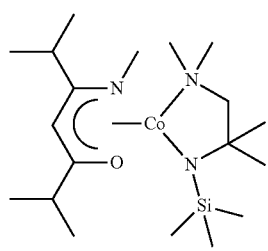
(1BC-91)
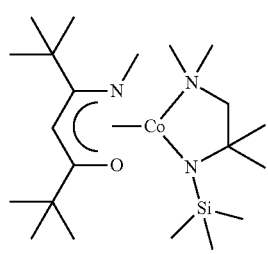
(1BC-92)
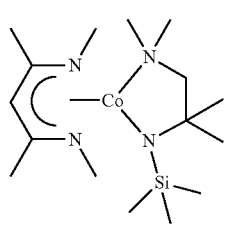
(1BC-93)
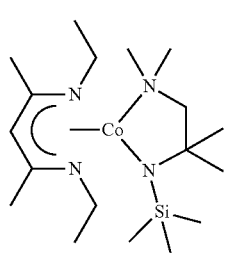
(1BC-94)
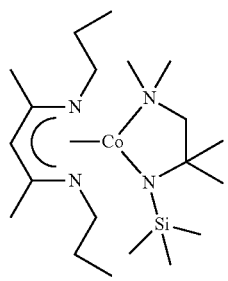
(1BC-95)
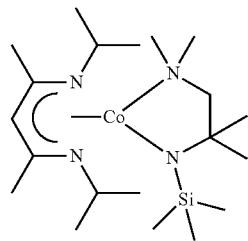
(1BC-96)
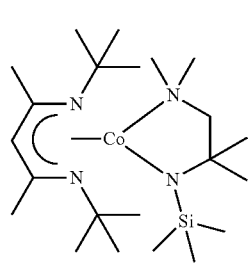
(1BC-97)
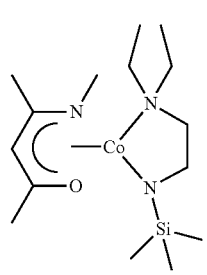
(1BC-98)
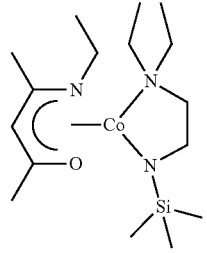
(1BC-99)
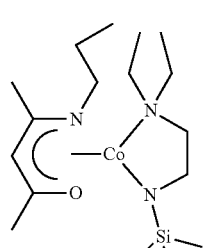
(1BC-100)
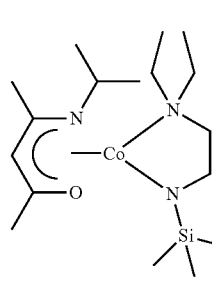

(1BC-101)
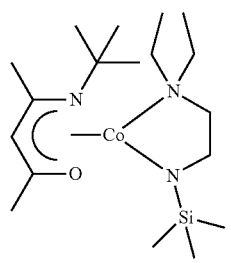
(1BC-102)
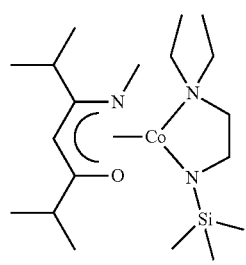
(1BC-103)
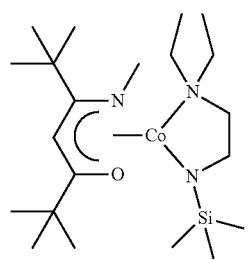
(1BC-104)
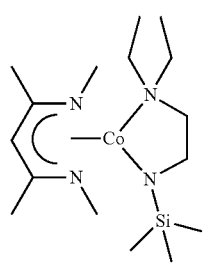
(1BC-105)
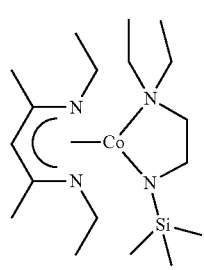
(1BC-106)
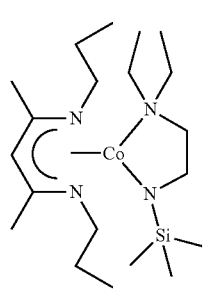
(1BC-107)
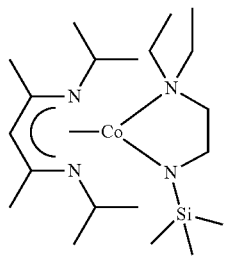
(1BC-108)
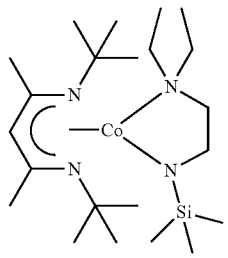
(1BC-109)
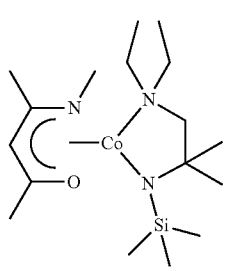
(1BC-110)
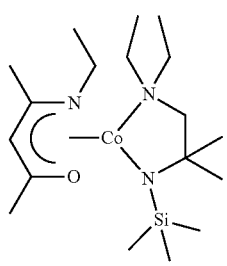
(1BC-111)
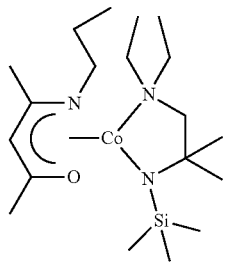
(1BC-112)
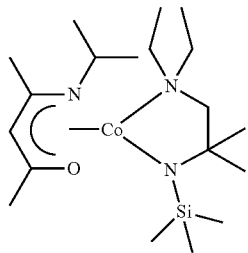

(1BC-113) 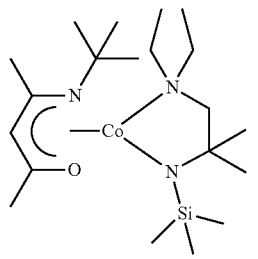

(1BC-114) 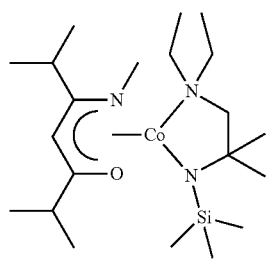

(1BC-115) 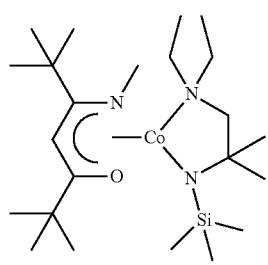

(1BC-116) 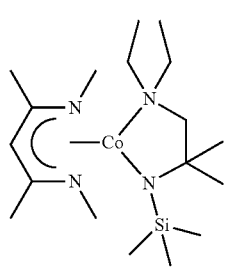

(1BC-117) 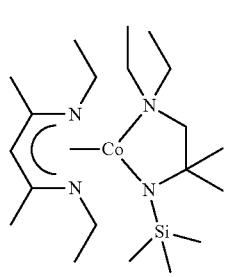

(1BC-118) 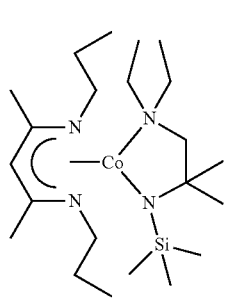

(1BC-119) 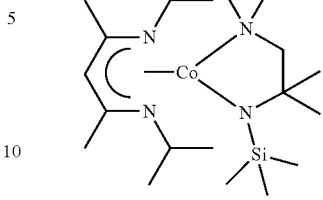

(1BC-120) 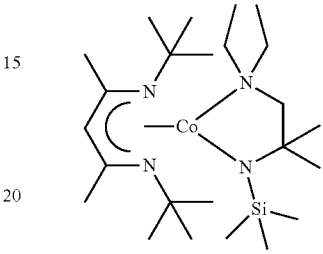

(1BC-1) to (1 BC-4), (1 BC-19) to (1 BC-22), (1 BC-55) to (1 BC-58), (1 BC-80) to (1 BC-84) and (1 BC-92) to (1 BC-96) are preferred, (1 BC-55) to (1BC-58) are more preferred, (1 BC-56) is further preferred, which have an appropriate vapor pressure and thermal stability as the CVD material and the ALD material.

Now, the method for producing the cobalt complex (1) will be described.

Among the cobalt complexes (1), the cobalt complexes (1AB), (1AC) and (1 BC) may be produced respectively by Production Methods 1, 2 and 3.

Production Method 1 is a method for producing the cobalt complex (1AB), which comprises reacting a bisamide complex (2) and an aminoalkylamine (3).

Production Method 1

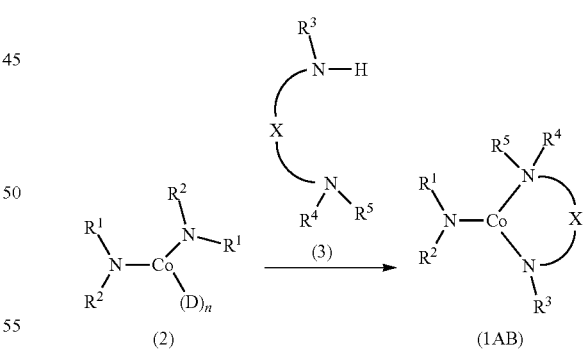

wherein $R^1$, $R^2$, $R^3$, $R^4$, $R^5$ and X are as defined above, D represents a neutral ligand, and n represents 0 or 1.

First, definition of D represented by the formula (2) will be described. D represents a neutral ligand and may, for example, be tetrahydrofuran (THF), a primary aliphatic amine such as methylamine, ethylamine, propylamine, isopropylamine, butylamine, isobutylamine, sec-butylamine or tert-butylamine, a secondary aliphatic amine such as dimethylamine or diethylamine, a tertiary aliphatic amine such as trimethylamine, ethyldimethylamine, diethylmethylamine or triethylamine, or a substituted/non-substituted pyridine such as pyridine or 4-dimethylaminopyridine. In view of high yield, THF or a tertiary aliphatic amine is preferred, THF or triethylamine is more preferred, and THF is further preferred.

n in the formula (2) represents 0 or 1.

As examples of the bisamide complex (2) used in Production Method 1, the following may be mentioned.

(2-1)
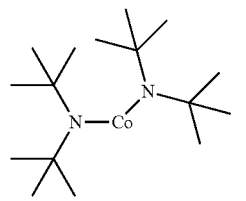

(2-2)
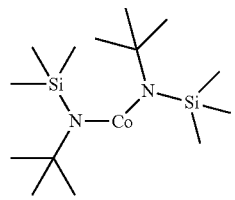

(2-3)
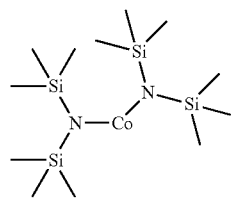

(2-4)
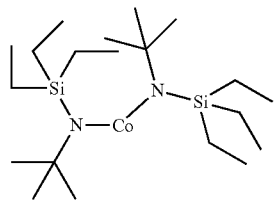

(2-5)
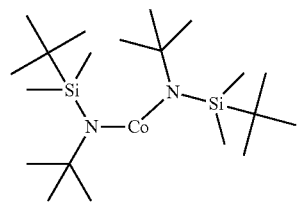

(2-6)
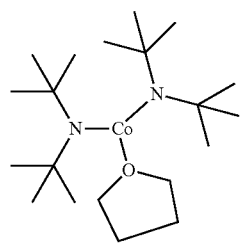

(2-7)
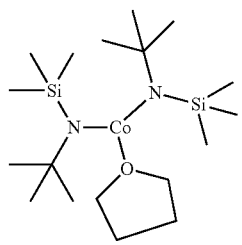

(2-8)
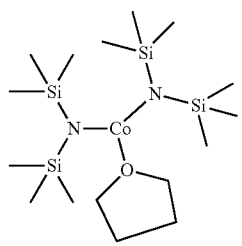

(2-9)
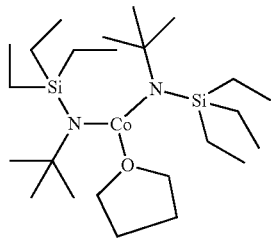

(2-10)
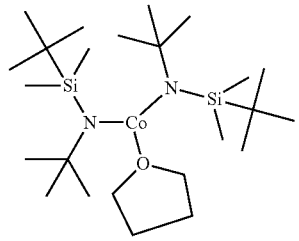

(2-11)
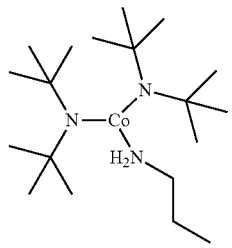

(2-12)
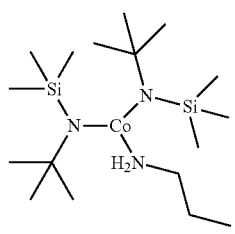

(2-13)
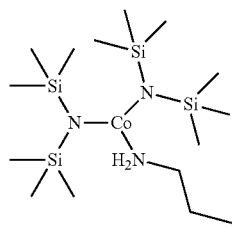
(2-14)
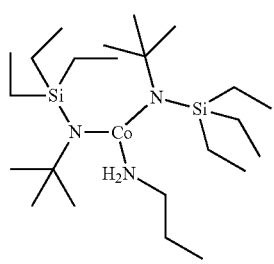
(2-15)
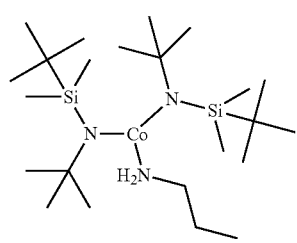
(2-16)
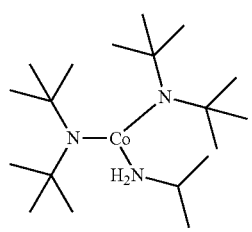
(2-17)
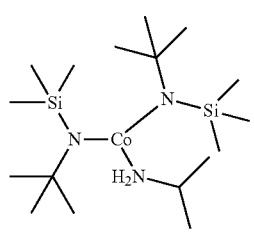
(2-18)
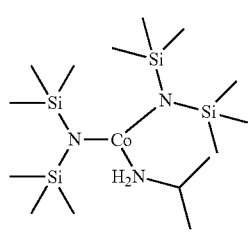
(2-19)
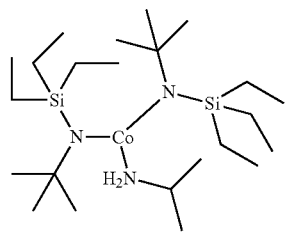
(2-20)
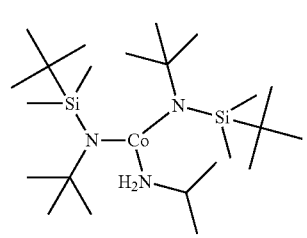
(2-21)
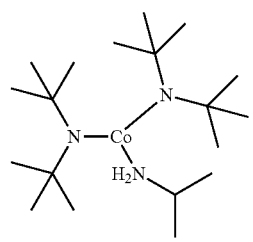
(2-22)
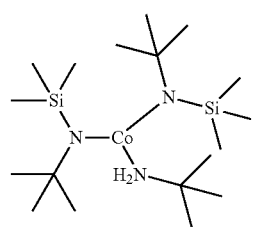
(2-23)
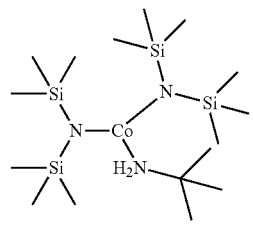
(2-24)
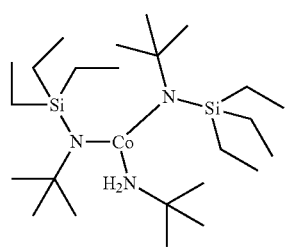

-continued
(2-25)
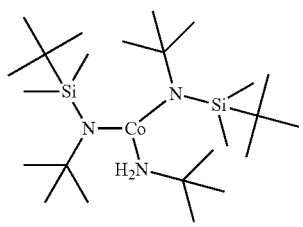
(2-26)
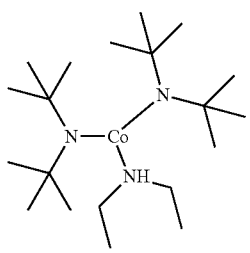
(2-27)
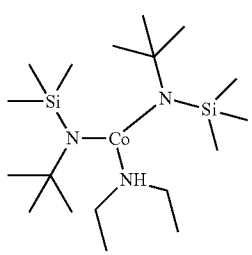
(2-28)
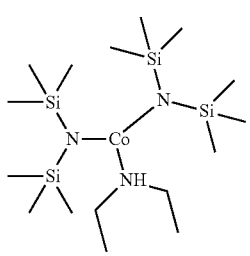
(2-29)
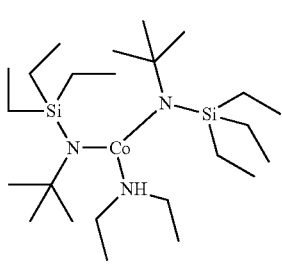
(2-30)
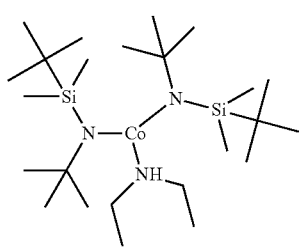
-continued
(2-31)
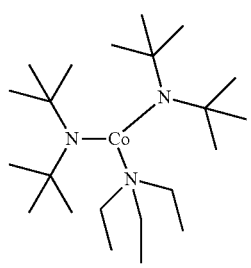
(2-32)
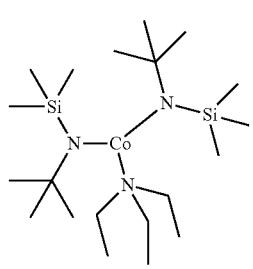
(2-33)
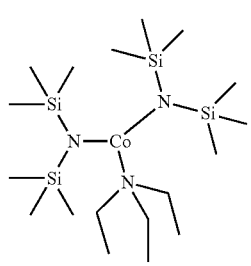
(2-34)
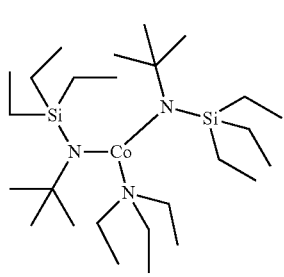
(2-35)
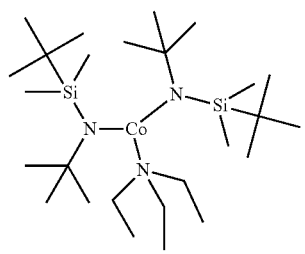
(2-36)
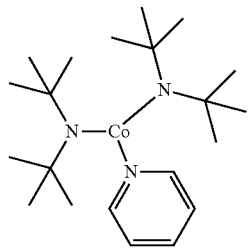

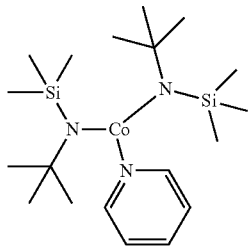

(2-37)

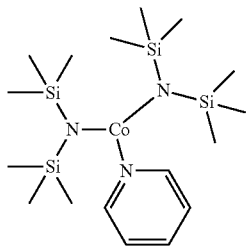

(2-38)

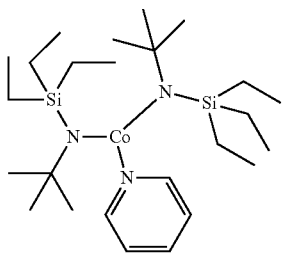

(2-39)

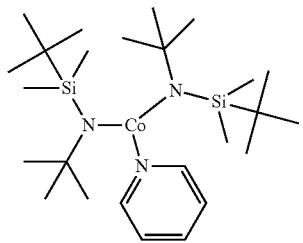

(2-40)

In view of high yield, (2-2), (2-3), (2-7) or (2-8) is preferred, (2-2), (2-3) or (2-8) is more preferred.

The bisamide complex (2) used in Production Method 1 may be obtained in accordance with the method disclosed in e.g. Inorganic Chemistry, vol. 53, 1962 (2014).

As examples of the aminoalkylamine (3) used in Production Method 1, [2-(dimethylamino)ethyl](trimethylsilyl)amine, [2-(diethylamino)ethyl](trimethylsilyl)amine, (trimethylsilyl)[2-(dipropylamino)ethyl]amine, [2-(dibutylamino)ethyl](trimethylsilyl)amine, (ethyldimethylsilyl)[2-(dimethylamino)ethyl]amine, [2-(diethylamino)ethyl](ethyldimethylsilyl)amine, (ethyldimethylsilyl)[2-(dipropylamino)ethyl]amine, [2-(dibutylamino)ethyl](ethyldimethylsilyl)amine, (diethylmethylsilyl)[2-(dimethylamino)ethyl]amine, [2-(diethylamino)ethyl](diethylmethylsilyl)amine, [2-(dipropylamino)ethyl](diethylmethylsilyl)amine, [2-(dibutylamino)ethyl](diethylmethylsilyl)amine, (triethylsilyl)[2-(dimethylamino)ethyl]amine, [2-(diethylamino)ethyl](triethylsilyl)amine, [2-(dipropylamino)ethyl](triethylsilyl)amine, [2-(dibutylamino)ethyl](triethylsilyl)amine, (tert-butyldimethylsilyl)[2-(dimethylamino)ethyl]amine, [2-(diethylamino)ethyl](tert-butyldimethylsilyl)amine, [2-(dipropylamino)ethyl](tert-butyldimethylsilyl)amine, [2-(dibutylamino)ethyl](tert-butyldimethylsilyl)amine, (2-dimethylamino-1,1-dimethylethyl)(trimethylsilyl)amine, (2-diethylamino-1,1-dimethylethyl)(trimethylsilyl)amine, (trimethylsilyl)(2-dipropylamino-1,1-dimethylethyl)amine, (2-dibutylamino-1,1-dimethylethyl)(trimethylsilyl)amine, (ethyldimethylsilyl)(2-dimethylamino-1,1-dimethylethyl)amine, (ethyldimethylsilyl)(2-diethylamino-1,1-dimethylethyl)amine, (ethyldimethylsilyl)(2-dipropylamino-1,1-dimethylethyl)amine, (ethyldimethylsilyl)(2-dibutylamino-1,1,-dimethylethyl)amine, (diethylmethylsilyl)(2-dimethylamino-1,1-dimethylethyl)amine, (diethylmethylsilyl)(2-diethylamino-1,1-dimethylethyl)amine, (diethylmethylsilyl)(2-dipropylamino-1,1-dimethylethyl)amine, (diethylmethylsilyl)(2-dibutylamino-1,1-dimethylethyl)amine, (triethylsilyl)(2-dimethylamino-1,1-dimethylethyl)amine, (triethylsilyl)(2-diethylamino-1,1-dimethylethyl)amine, (triethylsilyl)(2-dipropylamino-1,1-dimethylethyl)amine, (triethylsilyl)(2-dibutylamino-1,1-dimethylethyl)amine, (tert-butyldimethylsilyl)(2-dimethylamino-1,1-dimethylethyl)amine, (tert-butyldimethylsilyl)(2-diethylamino-1,1-dimethylethyl)amine, (tert-butyldimethylsilyl)(2-dipropylamino-1,1-dimethylethyl)amine, (tert-butyldimethylsilyl)(2-dibutylamino-1,1-dimethylethyl)amine, (2-dimethylamino-1,1-diethylethyl)(trimethylsilyl)amine, (2-diethylamino-1,1-diethylethyl)(trimethylsilyl)amine, (2-dipropylamino-1,1-diethylethyl)(trimethylsilyl)amine, (2-dibutylamino-1,1-diethylethyl)(trimethylsilyl)amine, (ethyldimethylsilyl)(2-dimethylamino-1,1-diethylethyl)amine, (2-diethylamino-1,1-diethylethyl)(ethyldimethylsilyl)amine, (ethyldimethylsilyl)(2-dipropylamino-1,1-diethylethyl)amine, (2-dibutylamino-1,1-diethylethyl)(ethyldimethylsilyl)amine, (diethylmethylsilyl)(2-dimethylamino-1,1-diethylethyl)amine, (2-diethylamino-1,1-diethylethyl)(diethylmethylsilyl)amine, (2-dipropylamino-1,1-diethylethyl)(diethylmethylsilyl)amine, (2-dibutylamino-1,1-diethylethyl)(diethylmethylsilyl)amine, (triethylsilyl)(2-dimethylamino-1,1-diethylethyl)amine, (2-diethylamino-1,1-diethylethyl)(triethylsilyl)amine, (2-dipropylamino-1,1-diethylethyl)(triethylsilyl)amine, (2-dibutylamino-1,1-diethylethyl)(triethylsilyl)amine, (tert-butyldimethylsilyl)(2-dimethylamino-1,1-diethylethyl)amine, (tert-butyldimethylsilyl)(2-diethylamino-1,1-diethylethyl)amine, (tert-butyldimethylsilyl)(2-dipropylamino-1,1-diethylethyl)amine, (tert-butyldimethylsilyl)(2-dibutylamino-1,1-diethylethyl)amine, [3-(dimethylamino)propyl](trimethylsilyl)amine, [3-(diethylamino)propyl](trimethylsilyl)amine may, for example, be mentioned. In view of high yield, [2-(dimethylamino)ethyl](trimethylsilyl)amine, (2-dimethylamino-1,1-dimethylethyl)(trimethylsilyl)amine or (2-diethylamino-1,1-dimethylethyl)(trimethylsilyl)amine is preferred, and (2-dimethylamino-1,1-dimethylethyl)(trimethylsilyl)amine is more preferred.

The aminoalkylamine (3) used in Production Method 1 may be obtained in accordance with the method as disclosed in e.g. JP-A-2016-222568.

The molar ratio of the aminoalkylamine (3) to the bisamide complex (2) in Production Method 1 is not particularly limited, and in view of high yield of the cobalt complex (1AB), the molar ratio of the aminoalkylamine (3) is preferably from 0.9 to 1.5 molar equivalent, more preferably from 1.0 to 1.2 molar equivalent, per molar equivalent of the bisamide complex (2).

Production Method 1 is preferably carried out in an inert gas atmosphere in view of high yield of the cobalt complex (1AB). The inert gas may, for example, be specifically helium, neon, argon, krypton, xenon or nitrogen gas. Nitrogen gas or argon is preferred, which is available at a low cost.

Production Method 1 is preferably carried out in an organic solvent in view of high yield of the cobalt complex (1AB). The organic solvent used is not particularly limited. It may, for example, be an aliphatic hydrocarbon such as pentane, hexane, heptane, octane, cyclohexane, methylcyclohexane, ethylcyclohexane or petroleum ether, an aromatic hydrocarbon such as benzene, toluene, xylene, ethylbenzene, propylbenzene, isopropylbenzene, butylbenzene, 2-methylpropylbenzene, 1-methylpropylbenzene, tert-butylbenzene or 1,3,5-trimethylbenzene (mesitylene), or an ether such as diethyl ether, diisopropyl ether, dibutyl ether, cyclopentyl methyl ether (CPME), cyclopentyl ethyl ether (CPEE), tert-butyl methyl ether (MTBE), THF, dioxane or 1,2-dimethoxyethane. Such organic solvents may be used as mixed in an optional proportion. In view of high yield of the cobalt complex (1AB), the organic solvent is preferably hexane, heptane, toluene or ether, more preferably hexane.

In Production Method 1, the reaction temperature and the reaction time are not particularly limited, and conventional conditions for producing an organic metal complex may be employed. As a specific example, at a reaction temperature properly selected from −80° C. to 120° C. for a reaction time properly selected within a range of from 10 minutes to 120 hours, the cobalt complex (1AB) can be produced with high yield.

The cobalt complex (1AB) produced by Production Method 1 may be purified by properly selecting a conventional purification method to purify an organic metal complex. As a specific purification method, filtration, extraction, centrifugal separation, decantation, distillation, sublimation or crystallization may, for example, be mentioned.

Production Method 2 is a method for producing the cobalt complex (1AC), which comprises reacting the bisamide complex (2) and a hetero atom-containing compound (4).

Production Method 2

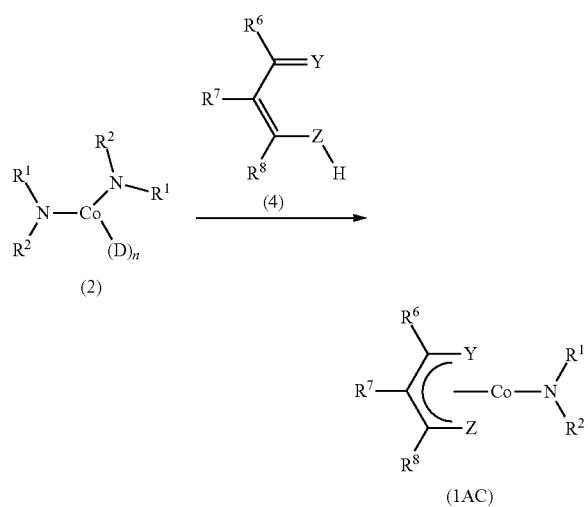

wherein $R^1$, $R^2$, $R^6$, $R^7$, $R^8$, Y, Z, D and n are as defined above.

As the bisamide complex (2) used in Production Method 2, the bisamide complex (2) described for Production Method 1 may be used.

The hetero atom-containing compound (4) may be not only one having a structure represented by the formula (4) but also tautomers represented by the formulae (4a) and (4b), and may be a mixture of two or more of (4), (4a) and (4b).

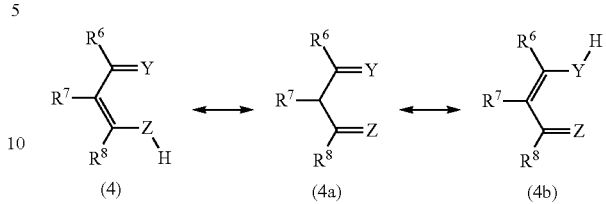

wherein $R^6$, $R^7$, $R^8$, Y and Z are as defined above.

In this specification, for simplification, the formulae (4), (4a) and (4b) are generally represented by the formula (4).

As examples of the hetero atom-containing compound (4) used in Production Method 2, pentane-2,4-dione, hexane-2,4-dione, heptane-2,4-dione, heptane-3,5-dione, octane-2,4-dione, octane-3,5-dione, nonane-2,4-dione, nonane-3,5-dione, nonane-4,6-dione, decane-2,4-dione, decane-3,5-dione, decane-4,6-dione, 5-methylhexane-2,4-dione, 5-methylheptane-2,4-dione, 2-methylheptane-3,5-dione, 2,6-dimethylheptane-3,5-dione, 2,2,6-trimethylheptane-3,5-dione, 2,2,6,6-tetramethylheptane-3,5-dione (dipivaloylmethane), 3-methylpentane-2,4-dione, 3-ethylpentane-2,4-dione, 3-propylpentane-2,4-dione, 3-isopropylpentane-2,4-dione, 3-butylpentane-2,4-dione, 3-isobutylpentane-2,4-dione, 3-sec-butylpentane-2,4-dione, 3-tert-butylpentane-2,4-dione, 4-(methylamino)-3-penten-2-one, 4-(ethylamino)-3-penten-2-one, 4-(propylamino)-3-penten-2-one, 4-(isopropylamino)-3-penten-2-one, 4-(butylamino)-3-penten-2-one, 4-(isobutylamino)-3-penten-2-one, 4-(sec-butylamino)-3-penten-2-one, 4-(tert-butylamino)-3-penten-2-one, 4-(methylamino)-3-hexen-2-one, 4-(ethylamino)-3-hexen-2-one, 4-(propylamino)-3-hexen-2-one, 4-(isopropylamino)-3-hexen-2-one, 4-(butylamino)-3-hexen-2-one, 4-(isobutylamino)-3-hexen-2-one, 4-(sec-butylamino)-3-hexen-2-one, 4-(tert-butylamino)-3-hexen-2-one, 5-(methylamino)-4-hexen-3-one, 5-(ethylamino)-4-hexen-3-one, 5-(propylamino)-4-hexen-3-one, 5-(isopropylamino)-4-hexen-3-one, 5-(butylamino)-4-hexen-3-one, 5-(isobutylamino)-4-hexen-3-one, 5-(sec-butylamino)-4-hexen-3-one, 5-(tert-butylamino)-4-hexen-3-one, 5-(methylamino)-4-hepten-3-one, 5-(ethylamino)-4-hepten-3-one, 5-(propylamino)-4-hepten-3-one, 5-(isopropylamino)-4-hepten-3-one, 5-(butylamino)-4-hepten-3-one, 5-(isobutylamino)-4-hepten-3-one, 5-(sec-butylamino)-4-hepten-3-one, 5-(tert-butylamino)-4-hepten-3-one, 2,6-dimethyl-5-(methylamino)-4-hepten-3-one, 2,6-dimethyl-5-(ethylamino)-4-hepten-3-one, 2,6-dimethyl-5-(propylamino)-4-hepten-3-one, 2,6-dimethyl-5-(isopropylamino)-4-hepten-3-one, 2,6-dimethyl-5-(butylamino)-4-hepten-3-one, 2,6-dimethyl-5-(isobutylamino)-4-hepten-3-one, 2,6-dimethyl-5-(sec-butylamino)-4-hepten-3-one, 2,6-dimethyl-5-(tert-butylamino)-4-hepten-3-one, 2,2,6,6-tetramethyl-5-(methylamino)-4-hepten-3-one, 2,2,6,6-tetramethyl-5-(ethylamino)-4-hepten-3-one, 2,2,6,6-tetramethyl-5-(propylamino)-4-hepten-3-one, 2,2,6,6-tetramethyl-5-(isopropylamino)-4-hepten-3-one, 2,2,6,6-tetramethyl-5-(butylamino)-4-hepten-3-one, 2,2,6,6-tetramethyl-5-(isobutylamino)-4-hepten-3-one, 2,2,6,6-tetramethyl-5-(sec-butylamino)-4-hepten-3-one, 2,2,6,6-tetramethyl-5-(tert-butylamino)-4-hepten-3-one, 2,2-dimethyl-5-(methylamino)-4-hepten-3-one, 2,2-dimethyl-5-(ethylamino)-4-hepten-3-one, 2,2-dimethyl-5-(propylamino)-4-hepten-3-one, 2,2-dimethyl-5-(isopropylamino)-4-hepten-3-one, 2,2-dimethyl-5-

(butylamino)-4-hepten-3-one, 2,2-dimethyl-5-(isobutylamino)-4-hepten-3-one, 2,2-dimethyl-5-(sec-butylamino)-4-hepten-3-one, 2,2-dimethyl-5-(tert-butylamino)-4-hepten-3-one, N-methyl-4-(methylimino)-2-penten-2-amine, N-methyl-4-(ethylimino)-2-penten-2-amine, N-methyl-4-(propylimino)-2-penten-2-amine, N-methyl-4-(isopropylimino)-2-penten-2-amine, N-methyl-4-(butylimino)-2-penten-2-amine, N-methyl-4-(isobutylimino)-2-penten-2-amine, N-methyl-4-(sec-butylimino)-2-penten-2-amine, N-methyl-4-(tert-butylimino)-2-penten-2-amine, N-ethyl-4-(ethylimino)-2-penten-2-amine, N-ethyl-4-(propylimino)-2-penten-2-amine, N-ethyl-4-(isopropylimino)-2-penten-2-amine, N-ethyl-4-(butylimino)-2-penten-2-amine, N-ethyl-4-(isobutylimino)-2-penten-2-amine, N-ethyl-4-(sec-butylimino)-2-penten-2-amine, N-ethyl-4-(tert-butylimino)-2-penten-2-amine, N-propyl-4-(propylimino)-2-penten-2-amine, N-propyl-4-(isopropylimino)-2-penten-2-amine, N-propyl-4-(butylimino)-2-penten-2-amine, N-propyl-4-(isobutylimino)-2-penten-2-amine, N-propyl-4-(sec-butylimino)-2-penten-2-amine, N-propyl-4-(tert-butylimino)-2-penten-2-amine, N-isopropyl-4-(isopropylimino)-2-penten-2-amine, N-isopropyl-4-(butylimino)-2-penten-2-amine, N-isopropyl-4-(isobutylimino)-2-penten-2-amine, N-isopropyl-4-(sec-butylimino)-2-penten-2-amine, N-isopropyl-4-(tert-butylimino)-2-penten-2-amine, N-butyl-4-(butylimino)-2-penten-2-amine, N-butyl-4-(isobutylimino)-2-penten-2-amine, N-butyl-4-(sec-butylimino)-2-penten-2-amine, N-butyl-4-(tert-butylimino)-2-penten-2-amine, N-isobutyl-4-(isobutylimino)-2-penten-2-amine, N-isobutyl-4-(sec-butylimino)-2-penten-2-amine, N-isobutyl-4-(tert-butylimino)-2-penten-2-amine, N-sec-butyl-4-(sec-butylimino)-2-penten-2-amine, N-sec-butyl-4-(tert-butylimino)-2-penten-2-amine, and N-tert-butyl-4-(tert-butylimino)-2-penten-2-amine may, for example, be mentioned.

In view of high yield, 2,2,6,6-tetramethylheptane-3,5-dione, 4-(methylamino)-3-penten-2-one, 4-(ethylamino)-3-penten-2-one, 4-(propylamino)-3-penten-2-one, 4-(isopropylamino)-3-penten-2-one, 4-(butylamino)-3-penten-2-one, 4-(tert-butylamino)-3-penten-2-one, N-methyl-4-(methylimino)-2-penten-2-amine, N-ethyl-4-(ethylimino)-2-penten-2-amine, N-propyl-4-(propylimino)-2-penten-2-amine, N-isopropyl-4-(isopropylimino)-2-penten-2-amine, N-butyl-4-(butylimino)-2-penten-2-amine, and N-tert-butyl-4-(tert-butylimino)-2-penten-2-amine are preferred, N-methyl-4-(methylimino)-2-penten-2-amine, N-ethyl-4-(ethylimino)-2-penten-2-amine, N-propyl-4-(propylimino)-2-penten-2-amine, N-isopropyl-4-(isopropylimino)-2-penten-2-amine, N-butyl-4-(butylimino)-2-penten-2-amine, and N-tert-butyl-4-(tert-butylimino)-2-penten-2-amine are more preferred, and N-propyl-4-(propylimino)-2-penten-2-amine is especially preferred.

The hetero atom-containing compound (4) used in Production Method 2 may be available as commercial products or may be obtained in accordance with the method as disclosed in e.g. The Journal of Organic Chemistry, Vol. 27, 1036 (1962), Tetrahedron Letters, Vol. 48, 8281 (2007), The Journal of Organic Chemistry, Vol. 73, 8673 (2008), or Dalton Transactions Vol. 42, 11,295 (2013).

The molar ratio of the hetero atom-containing compound (4) to the bisamide complex (2) in Production Method 2 is not particularly limited, and in view of high yield of the cobalt complex (1AC), the molar ratio of the hetero atom-containing compound (4) is preferably from 0.9 to 1.5 molar equivalent, more preferably from 1.0 to 1.2 molar equivalent, per 1 molar equivalent of the bisamide complex (2).

Production Method 2 is preferably carried out in an inert gas atmosphere in view of high yield of the cobalt complex (1AC). The inert gas may, for example, be specifically helium, neon, argon, krypton, xenon or nitrogen gas. Nitrogen gas or argon is preferred, which is available at a low cost.

Production Method 2 is preferably carried out in an organic solvent in view of high yield of the cobalt complex (1AC). The organic solvent used is not particularly limited. It may, for example, be an aliphatic hydrocarbon such as pentane, hexane, heptane, octane, cyclohexane, methylcyclohexane, ethylcyclohexane or petroleum ether, an aromatic hydrocarbon such as benzene, toluene, xylene, ethylbenzene, propylbenzene, isopropylbenzene, butylbenzene, 2-methylpropylbenzene, 1-methylpropylbenzene, tert-butylbenzene or 1,3,5-trimethylbenzene (mesitylene), or an ether such as diethyl ether, diisopropyl ether, dibutyl ether, CPME, CPEE, MTBE, THF, dioxane or 1,2-dimethoxyethane. Such organic solvents may be used as mixed in an optional proportion. In view of high yield of the cobalt complex (1AC), the organic solvent is preferably hexane, heptane, toluene or ether, more preferably CPME, MTBE, diethyl ether or THF.

In Production Method 2, the reaction temperature and the reaction time are not particularly limited, and conventional conditions for producing an organic metal complex may be employed. As a specific example, at a reaction temperature properly selected from −80° C. to 120° C. for a reaction time properly selected within a range of from 10 minutes to 120 hours, the cobalt complex (1AC) can be produced with high yield.

The cobalt complex (1AC) produced by Production Method 2 may be purified by properly selecting a conventional purification method to purify an organic metal complex. As a specific purification method, filtration, extraction, centrifugal separation, decantation, distillation, sublimation or crystallization may, for example, be mentioned.

Production Method 3 is a method for producing the cobalt complex (1 BC), which comprises reacting the cobalt complex (1AB) and the hetero atom-containing compound (4).

Production Method 3

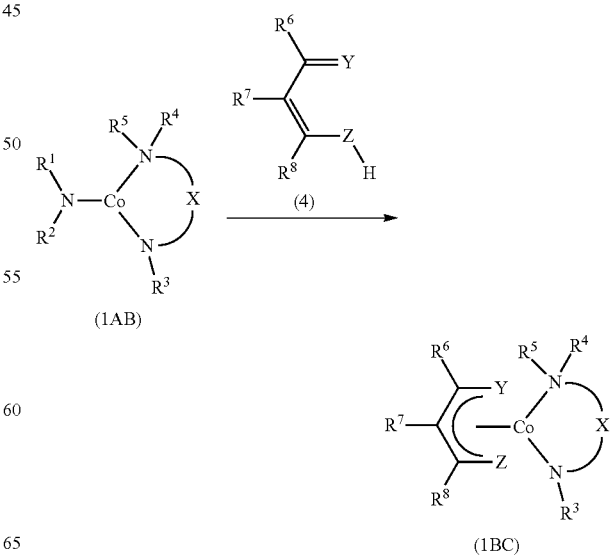

wherein $R^1$, $R^2$, $R^3$, $R^4$, $R^5$, $R^6$, $R^7$, $R^8$, X, Y and Z are as defined above.

The cobalt complex (1AB) used in Production Method 3 may be produced by the above Production Method 1.

In Production Method 3, the cobalt complex (1AB) may be used as the material without being purified, or the cobalt complex (1AB) purified by a conventional purification method for a metal complex may be used as the material. As a specific purification method, filtration, extraction, centrifugal separation, decantation, sublimation or crystallization may, for example, be mentioned.

Of the hetero atom-containing compound (4) used in Production Method 3, the hetero atom-containing compound (4) described for Production Method 2 may be used. In view of high yield, acetylacetone, heptan-3,5-dione or 2,2,6,6-tetramethylheptane-3,5-dione is preferred, and 2,2,6,6-tetramethylheptane-3,5-dione is more preferred.

The molar ratio of the hetero atom-containing compound (4) to the cobalt complex (1AB) in Production Method 3 is not particularly limited, and in view of high yield of the cobalt complex (1 BC), the molar ratio of the hetero atom-containing compound (4) is preferably from 0.8 to 1.5 molar equivalent, more preferably from 0.9 to 1.1 molar equivalent per 1 molar equivalent of the cobalt complex (1AB).

Production Method 3 is preferably carried out in an inert gas atmosphere in view of high yield of the cobalt complex (1 BC). The inert gas may, for example, be specifically helium, neon, argon, krypton, xenon or nitrogen gas. Nitrogen gas or argon is preferred, which is available at a low cost.

Production Method 3 is preferably carried out in an organic solvent in view of high yield of the cobalt complex (1 BC). The organic solvent used is not particularly limited. It may, for example, be an aliphatic hydrocarbon such as pentane, hexane, heptane, octane, cyclohexane, methylcyclohexane, ethylcyclohexane or petroleum ether, an aromatic hydrocarbon such as benzene, toluene, xylene, ethylbenzene, propylbenzene, isopropylbenzene, butylbenzene, 2-methylpropylbenzene, 1-methylpropylbenzene, tert-butylbenzene or 1,3,5-trimethylbenzene (mesitylene), or an ether such as diethyl ether, diisopropyl ether, dibutyl ether, CPME, CPEE, MTBE, THF, dioxane or 1,2-dimethoxyethane. Such organic solvents may be used as mixed in an optional proportion. In view of high yield of the cobalt complex (1 BC), the organic solvent is preferably hexane, heptane, toluene or ether, more preferably CPME, MTBE, diethyl ether or THF.

In Production Method 3, the reaction temperature and the reaction time are not particularly limited, and conventional conditions for producing an organic metal complex may be employed. As a specific example, at a reaction temperature properly selected from −80° C. to 120° C. for a reaction time properly selected within a range of from 10 minutes to 120 hours, the cobalt complex (1 BC) can be produced with high yield.

The cobalt complex (1 BC) produced by Production Method 3 may be purified by properly selecting a conventional purification method to purify an organic metal complex. As a specific purification method, filtration, extraction, centrifugal separation, decantation, distillation, sublimation or crystallization may, for example, be mentioned.

Now, the method for producing a cobalt-containing thin film, which comprises using the cobalt complex (1) for a vapor deposition method based on a chemical reaction will be described in detail. In this specification, the vapor deposition method based on a chemical reaction means a method for producing a cobalt-containing thin film by decomposing the vaporized cobalt complex (1) on a substrate. Specifically, a CVD method such as thermal CVD method, plasma CVD method or photo CVD method, or ALD method may, for example, be mentioned. The CVD method is especially preferred in view of a favorable film deposition rate, and the ALD method is especially preferred in view of favorable step coverage. For example, in a case where a cobalt-containing thin film is to be produced by the CVD method or the ALD method, the cobalt complex (1) is vaporized and supplied to a reaction chamber, and the cobalt complex (1) is decomposed on a substrate provided in the reaction chamber, whereby a cobalt-containing thin film can be produced on the substrate. As a method of decomposing the cobalt complex (1), a conventional technique employed for producing a metal-containing thin film may be mentioned. Specifically, a method of reacting the cobalt complex (1) and a reactive gas or a method of applying heat, plasma, light or the like to the cobalt complex (1) may, for example, be mentioned.

In a case where a reactive gas is used, the reactive gas used may, for example, be a reducing gas or an oxidizing gas. The reactive gas is preferably a reducing gas, whereby deterioration of a substrate made of a material which is easily oxidized, such as a metal or a metal nitride, can be prevented. The reducing gas may, for example, be specifically ammonia, hydrogen, monosilane, hydrazine, formic acid, a borane-amine complex such as a borane-dimethylamine complex or a borane-trimethylamine complex, a chain unsaturated hydrocarbon such as 1-butene, 2-butene, 2-methylpropene, 1-pentene, 2-pentene, 2-methyl-1-butene, 2-methyl-2-butene, 3-methyl-1-butene, 1-hexene, 2-hexene, 3-hexene, 2-methyl-1-pentene, 2-methyl-2-pentene, 4-methyl-2-pentene, 4-methyl-1-pentene, 3-methyl-1-pentene, 3-methyl-2-pentene, 2-ethyl-1-butene, 2,3-dimethyl-1-butene, 2,3-dimethyl-2-butene, 3,3-dimethyl-1-butene, buta-1,3-diene, penta-1,3-diene, penta-1,4-diene, 2-methylbuta-1,3-diene, hexa-1,3-diene, hexa-2,4-diene, 2-methylpenta-1,3-diene, 3-methylpenta-1,3-diene, 4-methylpenta-1,3-diene, 2-ethylbuta-1,3-diene, 3-methylpenta-1,4-diene or 2,3-dimethylbuta-1,3-diene, or a cyclic unsaturated hydrocarbon such as cyclohexa-1,3-diene, cyclohexa-1,4-diene, 1-methylcyclohexa-1,3-diene, 2-methylcyclohexa-1,3-diene, 5-methylcyclohexa-1,3-diene, 3-methylcyclohexa-1,4-diene, α-phellandrene, β-phellandrene, α-terpinene, β-terpinene, γ-terpinene or limonene.

The reducing gas is preferably ammonia, hydrogen, formic acid, cyclohexa-1,3-diene, cyclohexa-1,4-diene, α-terpinene, β-terpinene, γ-terpinene or limonene, in view of loss restriction by the specifications of a film deposition apparatus and handling efficiency. In a case where an oxidizing gas is used, it may, for example, be specifically oxygen, ozone, water vapor, hydrogen peroxide, nitrous oxide, hydrogen chloride, nitric acid gas or acetic acid, and is preferably oxygen, ozone or water vapor. The flow rate of the reactive gas is properly adjusted depending upon the reactivity of the material and the capacity of the reaction chamber. For example, in a case where the capacity of the reaction chamber is from 1 to 10 L, the flow rate of the reactive gas is not particularly limited and is preferably from 1 to 10,000 sccm from economical reasons. In this specification, sccm is a unit representing the flow rate of a gas, and 1 sccm means that a gas moves at a rate of 2.68 mmol/h as calculated as ideal gas.

In a case where the cobalt-containing thin film is to be produced by the CVD method or the ALD method, a cobalt-containing thin film can be produced by properly selecting such a decomposition method. A plurality of decomposition methods may be used in combination. To supply the cobalt complex (1) to the reaction chamber, a conventional method, for example, bubbling or a liquid vaporizer system may be mentioned, and the method is not particularly limited.

In a case where a cobalt-containing thin film is to be produced by the CVD method or the ALD method, the carrier gas and the diluent gas are preferably a rare gas such as helium, neon, argon, crypton or xenon, or a nitrogen gas, and are more preferably nitrogen gas or argon from economical reasons. The flow rate of the carrier gas and the diluent gas is properly adjusted depending upon e.g. the capacity of the reaction chamber. For example, in a case where the capacity of the reaction chamber is from 1 to 10 L, the flow rate of the carrier gas is not particularly limited and is preferably from 1 to 10,000 sccm from economical reasons.

In a case where a cobalt-containing thin film is to be produced by the CVD method or the ALD method, the substrate temperature is properly selected depending upon e.g. whether heat, plasma, light or the like is used or not, or the type of the reactive gas. For example, in a case where ammonia is used as the reactive gas without using light or plasma in combination, the substrate temperature is not particularly limited and is preferably from 50° C. to 1,000° C. from economical reasons. In view of favorable film deposition rate, it is preferably from 100° C. to 300° C., more preferably from 150° C. to 250° C. Further, by properly using light, plasma, ozone, hydrogen peroxide or the like, the cobalt-containing thin film can be produced in a further lower temperature region.

When a cobalt-containing thin film is to be produced by the CVD method or the ALD method, the film deposition pressure is preferably reduced pressure, preferably from 1 to 100 Torr, more preferably from 1 to 10 Torr, in view of favorable uniformity of the film thickness, step coverage and film quality.

The cobalt-containing thin film obtained by the method for producing a cobalt-containing thin film of the present invention may, for example, be a metal cobalt thin film, a cobalt oxide thin film, a cobalt nitride thin film or a cobalt oxynitride thin film. Further, after production of a metal cobalt thin film, by subjecting the substrate to a heat treatment at an optional temperature, a cobalt-containing composite film may be obtained. For example, after a metal cobalt thin film is produced on a silicon substrate, a heat treatment at from 300° C. to 900° C. may be carried out to obtain a cobalt silicide thin film of e.g. $Co_2Si$, $CoSi$ or $CoSi_2$. Further, a cobalt-containing composite thin film can be obtained also by using other metal material in combination. For example, by using the cobalt complex (1) and a silicon material in combination, a cobalt silicide thin film will be obtained. The silicon material may, for example, be monosilane, disilane, trisilane, tetraethoxysilane, dimethyldimethoxysilane, bis(tert-butylamino)silane, bis(diethylamino)silane or tris(dimethylamino)silane. Further, by using the cobalt complex (1) in combination with a metal material containing a typical metal such as aluminum or germanium, a transition metal such as titanium, zirconium, hafnium, niobium, tantalum or tungsten, or a rare earth metal such as lanthanum or neodymium, a cobalt-containing composite film containing such a metal element can be obtained.

Further, in a case where a cobalt-containing composite thin film is produced by the CVD method or the ALD method, the cobalt complex (1) and other metal material may be supplied separately to the reaction chamber, or may be supplied as mixed.

By using the cobalt-containing thin film of the present invention as a constituting member, a high performance semiconductor device having improved reliability and responsibility can be produced. The semiconductor device may, for example, be a semiconductor storage device such as DRAM, FeRAM, PRAM, MRAM, ReRAM or Flash memory, or a field-effect transistor. The constituting member for such a device may, for example, be a gate electrode, contact on a diffusion layer between source and drain portions, or a copper wiring seed layer/liner layer/cap layer of a transistor.

EXAMPLES

Now, the present invention will be described in further detail with reference to Examples. However, it should be understood that the present invention is by no means restricted thereto. Production of compounds in Reference Examples 1 to 7 and Examples 1 to 7, 12 and 16 was carried out in an argon atmosphere. THF, diethyl ether and hexane used are dehydrated reagents manufactured by KANTO CHEMICAL CO., INC. 2-Dimethylamino-1,1-dimethylethylamine and 2-diethylamino-1,1-dimethylethylamine were prepared in accordance with the method disclosed in JP-A-2018-507255.

Reference Example 1

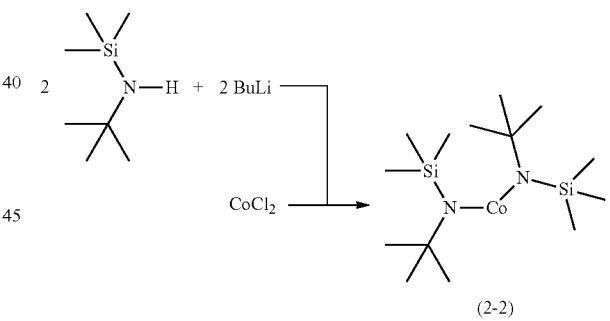

To a diethyl ether (60 mL) solution of 7.62 g (52.4 mmol) of (tert-butyl)(trimethylsilyl)amine, 36.0 mL (1.6 mol/L, 57.6 mmol) of a hexane solution of butyllithium was added at 0° C. The mixture was stirred at 25° C. for 2 hours and then added to a diethyl ether (30 mL) suspension of 3.40 g (26.2 mmol) of cobalt chloride at −78° C. The mixture was stirred at 25° C. for 18 hours, and then the solvent was distilled off under reduced pressure. 60 mL of hexane was added to the residue, followed by vigorous stirring at room temperature. The formed suspension was subjected to filtration, and the solvent was distilled off under reduced pressure from the filtrate. The remaining liquid was distilled (heating temperature: 90° C./back pressure: 39 Pa) to obtain 2.93 g (yield: 32%) of bis[(tert-butyl)(trimethylsilyl)amino] cobalt (2-2) as a dark red liquid.

$^1$H-NMR (400 MHz, $C_6D_6$, δ): 54.3 (br, 18H), 33.0 (br, 18H)

Reference Example 2

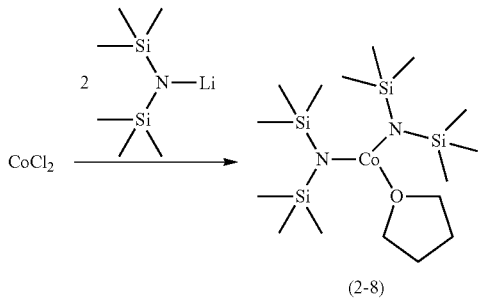

(2-8)

To a THF (50 mL) solution of 13.0 g (100 mmol) of cobalt chloride, 154 mL (1.3 mol/L, 200 mmol) of a THF solution of lithium bis(trimethylsilyl)amide was added at −78° C. The mixture was stirred at 25° C. for 17 hours, and the solvent was distilled off under reduced pressure. 90 mL of hexane was added to the residue, followed by vigorous stirring at room temperature. The formed suspension was subjected to filtration, and the solvent was distilled off under reduced pressure from the filtrate. The remaining solid was sublimated (heating temperature: 120° C./back pressure: 51 Pa) to obtain 40.1 g (yield: 89%) of bis[bis(trimethylsilyl) amino] cobalt (2-8) as a dark green solid.

$^1$H-NMR (400 MHz, $C_6D_6$, δ): 168.2 (br, 4H), 100.2 (br, 4H), −15.9 (br, 36H).

Reference Example 3

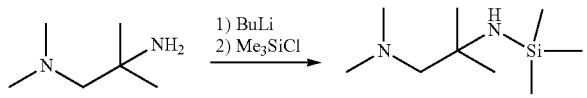

In 20 mL of THF, 4.95 g (42.6 mmol) of 2-dimethylamino-1,1-dimethylethylamine was dissolved, followed by cooling to −78° C., and 16 mL (2.65 mol/L, 42.4 mmol) of a hexane solution of butyllithium was added. The mixture was stirred at room temperature for 15 hours and cooled to 0° C., and 4.61 g of chlorotrimethylsilane was dropwise added over a period of 30 minutes. The mixture was stirred at room temperature for 4 hours, and the solvent was distilled off under normal pressure. From the obtained slurry, components soluble in hexane were extracted. The extract was concentrated and distilled under reduced pressure (distillation temperature: 80 to 82° C., back pressure: 40 Torr) to obtain 7.05 g (yield: 87%) of (2-dimethylamino-1,1-dimethylethyl)(trimethylsilyl)amine as a colorless liquid.

$^1$H-NMR (400 MHz, $CDCl_3$, δ): 2.32 (s, 6H), 2.11 (s, 2H), 1.09 (s, 6H), 1.05 (br, 1H), 0.06 (s, 9H).

Reference Example 4

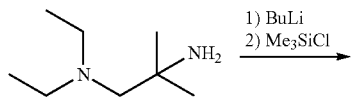

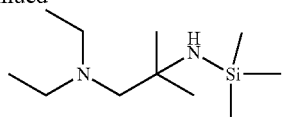

In 50 mL of THF, 17.0 g (118 mmol) of 2-diethylamino-1,1-dimethylethylamine was dissolved, followed by cooling to −78° C., and 45 mL (2.65 M, 119 mmol) of a hexane solution of butyllithium was added. The mixture was stirred at room temperature for 15 hours and cooled to 0° C., and 13.0 g of chlorotrimethylsilane was dropwise added over a period of 30 minutes. The mixture was stirred at room temperature for 6 hours, and the solvent was distilled off under normal pressure. From the obtained slurry, components soluble in hexane were extracted. The extract was concentrated and distilled under reduced pressure (distillation temperature: 105° C., back pressure: 38 Torr) to obtain 24.6 g (yield: 96%) of (2-diethylamino-1,1-dimethylethyl) (trimethylsilyl)amine as a colorless liquid.

$^1$H-NMR (400 MHz, $CDCl_3$, δ) 2.57 (q, J=7.1 Hz, 4H), 2.50 (br, 1H), 2.27 (s, 2H), 1.07 (s, 6H), 0.98 (t, J=7.1 Hz, 6H), 0.05 (s, 9H).

Reference Example 5

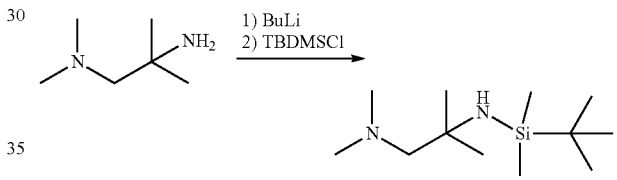

In 30 mL of THF, 6.80 g (58.5 mmol) of 2-dimethylamino-1,1-dimethylethylamine was dissolved, followed by cooling to −78° C., and 21.4 mL (2.76 M, 59.1 mmol) of a hexane solution of butyllithium was added. The mixture was stirred at room temperature for 16 hours and cooled to 0° C., and a THF (20 mL) solution of 10.8 g of tert-butylchlorodimethylsilane was dropwise added over a period of 30 minutes. The mixture was stirred at room temperature for 16 hours, and the solvent was distilled off under normal pressure. From the obtained slurry, components soluble in hexane were extracted. The extract was concentrated and distilled under reduced pressure (distillation temperature: 77° C., back pressure: 6 Torr) to obtain 11.0 g (yield: 81%) of (2-dimethylamino-1,1-dimethylethyl)(tert-butyldimethylsilyl)amine as a colorless liquid.

$^1$H-NMR (400 MHz, $CDCl_3$, δ) 2.31 (s, 6H), 2.10 (s, 2H), 1.07 (s, 6H), 1.01 (br, 1H), 0.86 (s, 9H), 0.03 (s, 6H).

Reference Example 6

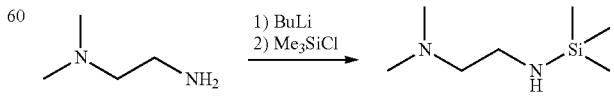

To 100 mL of THF, 19.7 g (223.8 mmol) of 2-dimethylaminoethylamine was dissolved, followed by cooling to −78° C., and 82 mL (2.76 M, 226.3 mmol) of a hexane solution of butyllithium was added. The mixture was stirred at room temperature for one hour and cooled to −78° C., and a hexane (50 mL) solution of 24.6 g of chlorotrimethylsilane was dropwise added over a period of 30 minutes. The mixture was stirred at room temperature for 16 hours, and the solvent was distilled off under normal pressure. From the obtained slurry, components soluble in hexane were extracted. The extract was concentrated and distilled under reduced pressure (distillation temperature: 72° C., back pressure: 56 Torr) to obtain 28.8 g (yield: 80%) of [2-(dimethylamino)ethyl](trimethylsilyl)amine as a colorless liquid.

$^{1}$H-NMR (400 MHz, C$_6$D$_6$, δ) 2.75 (dt, J=7.0, 6.1 Hz, 2H), 2.19 (t, J=6.1 Hz, 2H), 2.07 (s, 6H), 0.97 (br, 1H), 0.10 (s, 9H).

Reference Example 7

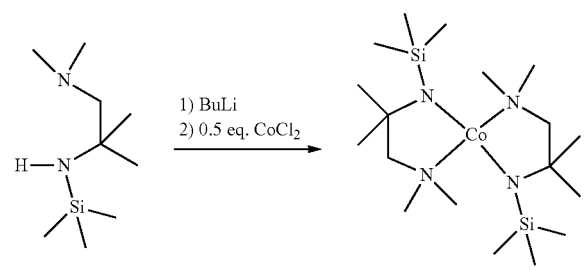

To a diethyl ether (40 mL) solution of 4.56 g (24.2 mmol) of (2-dimethylamino-1,1-dimethylethyl)(trimethylsilyl)amine prepared in Reference Example 3, 16.0 mL (1.6 mol/L, 25.6 mmol) of a hexane solution of butyllithium was added at 0° C. The mixture was stirred at 25° C. for one hour and added to a diethyl ether (20 mL) suspension of 1.50 g (11.6 mmol) of cobalt chloride at −78° C. The mixture was stirred at 25° C. for 18 hours, and the solvent was distilled off under reduced pressure. To the residue, 80 mL of hexane was added, followed by vigorous stirring at room temperature. The formed suspension was subjected to filtration, and the solvent was distilled off under reduced pressure from the filtrate. The remaining solid was sublimated (heating temperature: 160° C./back pressure: 39 Pa) to obtain 1.75 g (yield: 35%) of bis[(2-dimethylamino-1,1-dimethylethyl)(trimethylsilyl)amino] cobalt as a purple liquid.

$^{1}$H-NMR (400 MHz, C$_6$D$_6$, δ): 134.0 (brs, 12H), 102.9 (brs, 4H), 39.4 (brs, 12H), −27.8 (brs, 18H).

Example 1

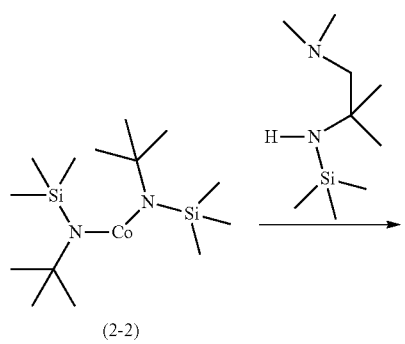

(2-2)

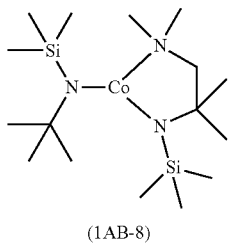

(1AB-8)

695 mg (3.69 mmol) of {1,1-dimethyl-2-(dimethylamino)ethyl}(trimethylsilyl)amine prepared in Reference Example 3 was added at 0° C. to a hexane (15 mL) solution of 1.52 g (4.37 mmol) of bis[(tert-butyl)(trimethylsilyl)amino] cobalt (2-2) prepared in Reference Example 1. The mixture was stirred at 25° C. for 2 hours, followed by heat reflux for 17 hours. The solvent was distilled off under reduced pressure from the obtained solution, and the remaining liquid was distilled (heating temperature: 130° C./back pressure: 47 Pa) to obtain 700 mg (yield: 49%) of [(tert-butyl)(trimethylsilyl)amino][(2-dimethylamino-1,1-dimethylethyl)(trimethylsilypamino] cobalt (1AB-8) as a dark green liquid.

$^{1}$H-NMR (400 MHz, C$_6$D$_6$, δ):189.0 (br, 2H), 122.0 (br, 3H), 111.1 (br, 3H), 84.6 (br, 3H), 58.7 (br, 3H), 36.0 (brs, 9H), 0.83 (brs, 9H), −6.21 (brs, 9H).

Example 2

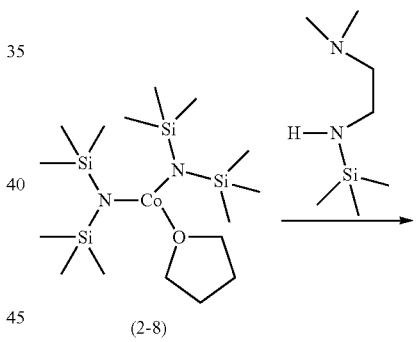

(2-8)

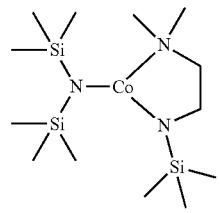

(1AB-13)

711 mg (4.43 mmol) of [2-(dimethylamino)ethyl](trimethylsilyl)amine prepared in Reference Example 6 was added at −78° C. to a THF (20 mL) solution of 1.98 g (4.38 mmol) of bis[bis(trimethylsilyl)amino] cobalt (2-8) prepared in Reference Example 2. The mixture was stirred at 25° C. for 17 hours, and the solvent was distilled off under reduced pressure. The remaining liquid was distilled (heating temperature: 100° C./back pressure: 50 Pa), to obtain 900 mg (yield: 54%) of {[2-(dimethylamino)ethyl](trimethylsilyl)amino}[bis(trimethylsilyl)amino] cobalt (1AB-13) as a dark green liquid.

¹H-NMR (400 MHz, C₆D₆, δ): 124.6 (brs, 6H), 107.5 (br, 2H), 68.4 (br, 2H), 12.7 (brs, 9H), −9.32 (brs, 18H).

Example 3

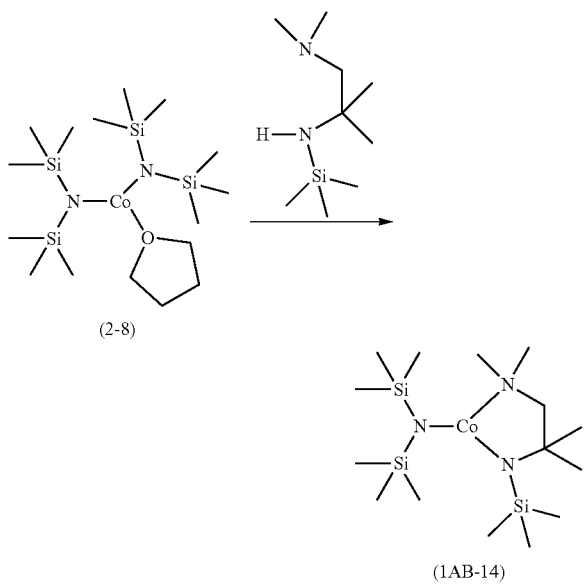

10.2 g (54.3 mmol) of (2-dimethylamino-1,1-dimethylethyl)(trimethylsilyl)amine prepared in Reference Example 3 was added at 25° C. to a hexane (50 mL) solution of 24.5 g (54.3 mmol) of bis[bis(trimethylsilyl)amino] cobalt (2-8) prepared in Reference Example 2. The mixture was stirred at 25° C. for one hour, followed by heat reflux for 18 hours. The solvent was distilled off under reduced pressure from the obtained solution, and the remaining liquid was distilled (heating temperature: 120° C./distillation temperature: 103° C./back pressure: 56 Pa) to obtain 19.7 g (yield: 89%) of [(2-dimethylamino-1,1-dimethylethyl)(trimethylsilyl)amino][bis(trimethylsilypamino] cobalt (1AB-14) as a dark green liquid.

¹H-NMR (400 MHz, C₆D₆, δ): 149.5 (brs, 6H), 118.7 (brs, 2H), 62.0 (brs, 6H), 32.7 (brs, 9H), −12.7 (brs, 18H).

Example 4

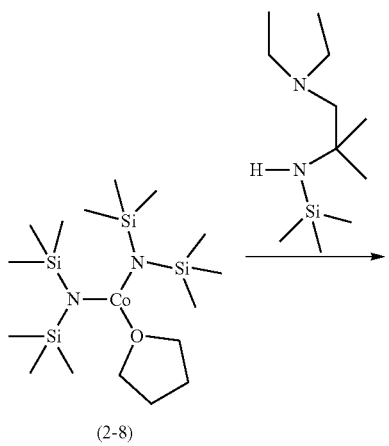

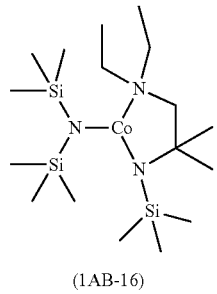

587 mg (2.71 mmol) of (2-diethylamino-1,1-dimethylethyl)(trimethylsilyl)amine prepared in Reference Example 4 was added at 0° C. to a hexane (10 mL) solution of 1.22 g (2.70 mmol) of bis[bis(trimethylsilyl)amino] cobalt (2-8) prepared in Reference Example 2. The mixture was stirred at 25° C. for one hour, followed by heat reflux for 18 hours. The solvent was distilled off under reduced pressure from the obtained solution, and the remaining liquid was distilled (heating temperature: 135° C./back pressure: 50 Pa) to obtain 440 mg (yield: 38%) of [(2-diethylamino-1,1-dimethylethyl)(trimethylsilyl)amino][bis(trimethylsilypamino] cobalt (1AB-16) as a dark green liquid.

¹H-NMR (400 MHz, C₆D₆, δ): 117.8 (br, 2H), 59.7 (brs, 6H), 27.6 (br, 4H), 20.5 (brs, 9H), 17.3 (brs, 6H), −12.8 (brs, 18H).

Example 5

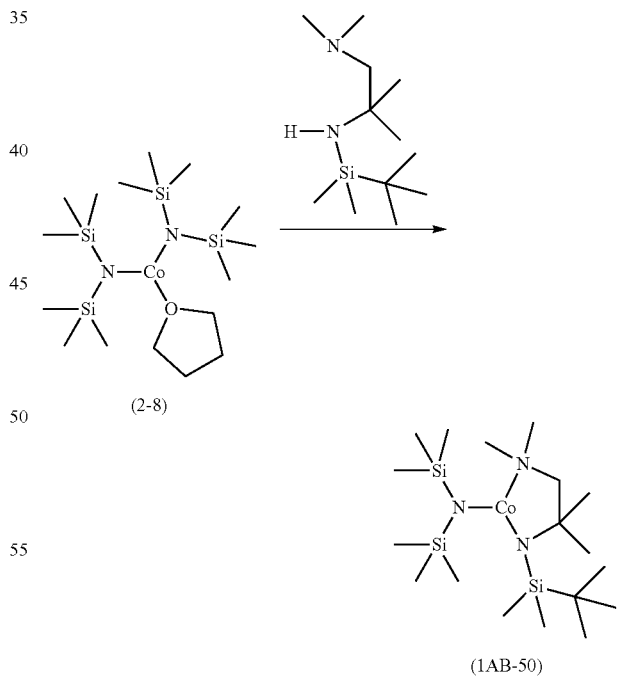

1.72 g (7.46 mmol) of (2-dimethylamino-1,1-dimethylethyl)(tert-butyldimethylsilyl)amine prepared in Reference Example 5 was added at 0° C. to a hexane (10 mL) solution of 3.39 g (7.50 mmol) of bis[bis(trimethylsilyl)amino] cobalt (2-8) prepared in Reference Example 2. The mixture was stirred at 25° C. for one hour, followed by heat reflux for 30 hours. The solvent was distilled off under reduced pressure from the obtained solution, and the remaining liquid was distilled (heating temperature: 135° C./back pressure: 43 Pa) to obtain 220 mg (yield: 7%) of [(2-dimethylamino-1,1-dimethylethyl)(tert-butyldimethylsilyl)amino][bis(trimethylsilyl)amino] cobalt (1AB-50) as a dark green liquid.

$^1$H-NMR (400 MHz, C$_6$D$_6$, δ): 160.4 (br, 6H), 116.0 (br, 2H), 62.5 (brs, 6H), 44.6 (brs, 6H), −6.60 (brs, 9H), −14.5 (brs, 18H).

Example 6

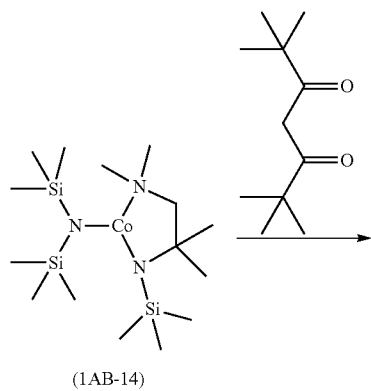

(1AB-14)

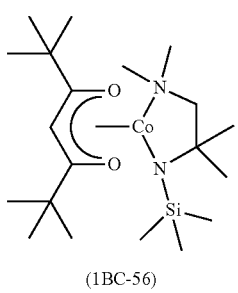

(1BC-56)

6.93 g (37.6 mmol) of dipivaloylmethane was added at 0° C. to a THF (80 mL) solution of 15.5 g (38.1 mmol) of [(2-dimethylamino-1,1-dimethylethyl)(trimethylsilyl)amino][bis(trimethylsilypamino] cobalt (1AB-14) prepared in Example 3. The mixture was stirred at 25° C. for 16 hours, and the solvent was distilled off under reduced pressure. The remaining liquid was distilled (heating temperature: 130° C./back pressure: 38 Pa) to obtain 7.3 g (yield: 45%) of [(2-dimethylamino-1,1-dimethylethyl)(trimethylsilyl)amino](2,2,6,6-tetramethyl-3,5-heptanedionate) cobalt (1BC-56) as a dark green liquid.

$^1$H-NMR (400 MHz, C$_6$D$_6$, δ): 65.6 (br, 6H), 53.8 (br, 1H), 46.1 (br, 1H), 40.3 (br, 6H), 14.2 (brs, 18H), 3.99 (br, 9H), −30.3 (br, 1H).

Example 7

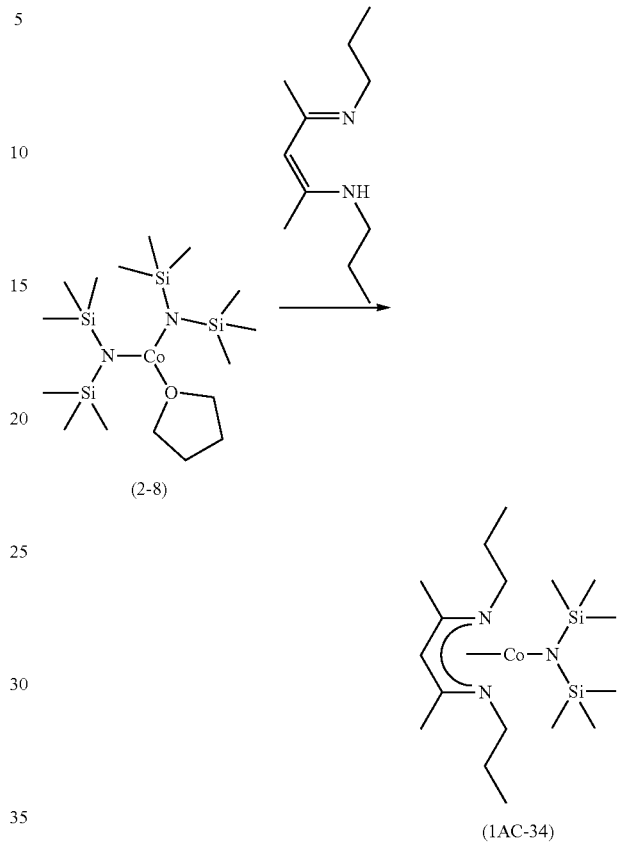

724 mg (3.97 mmol) of N-propyl-4-(propylimino)-2-pentene-2-amine prepared in accordance with the method disclosed in The Journal of Organic Chemistry, vol. 73, 8673 (2008) was added at 0° C. to a hexane (10 mL) solution of 3.38 g (7.48 mmol) of bis[bis(trimethylsilyl)amino] cobalt (2-8) prepared in Reference Example 2. The mixture was stirred at 25° C. for 19 hours, and the solvent was distilled off under reduced pressure. The remaining liquid was distilled (heating temperature: 125° C./back pressure: 56 Pa), to obtain 280 mg (yield: 17%) of [N-propyl-4-(propylimino)pent-2-ene-2-amino][bis(trimethylsilyl)amino] cobalt (1AC-34) as a dark red liquid.

$^1$H-NMR (400 MHz, C$_6$D$_6$, δ): 7.40 (brs, 6H), 3.05 (br, 4H), −2.33 (br, 4H), −5.90 (brs, 18H), −29.7 (brs, 6H), −88.0 (br, 1H).

Evaluation Example 1

Thermal Analysis of [(2-dimethylamino-1,1-dimethylethyl)(trimethylsilyl)amino][bis(trimethylsilypamino] cobalt (1AB-14)

As a sample, (1AB-14) prepared in Example 3 was used in amounts of 18.9 mg for thermogravimetry (TG) and 7.5 mg for differential scanning calorimetry (DSC).

Figure 2:
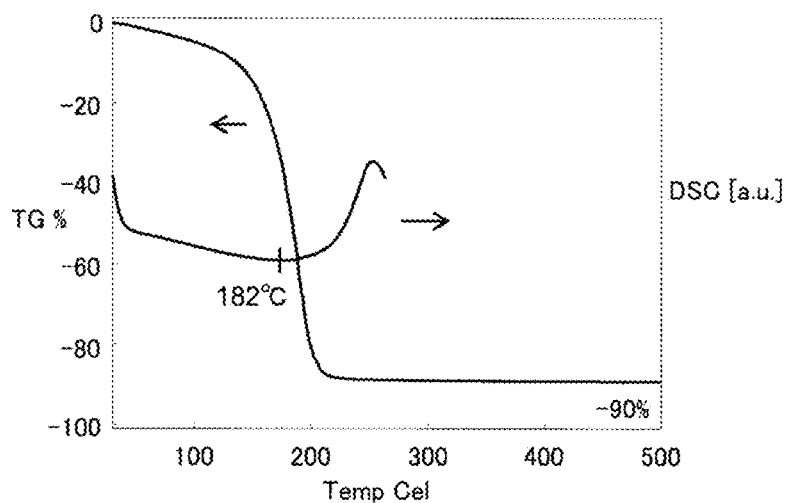
FIG. 2 is a TG and DSC chart of [(2-dimethylamino-1,1-dimethylethyl)(trimethylsilyl)amino][bis(trimethylsilylpamino] cobalt (1AB-14) in Evaluation Example 1.

The results of TG measured in an atmosphere in which argon flowed at 400 mL/min at a temperature-raising rate of 10° C./min, and the results of DSC measured in a sealed container at a temperature-raising rate of 10° C./min are shown in FIG. 2. It is found from TG that the residue by thermal decomposition is 10% and from DSC that the thermal decomposition starting temperature is 182° C. Further, no melting point measured in DSC proves that (1AB-14) is liquid at room temperature.

Evaluation Example 2

Thermal Analysis of [(2-dimethylamino-1,1-dimethylethyl)(trimethylsilyl)amino](2,2,6,6-tetramethyl-3,5-heptanedionate) cobalt (1 BC-56)

As a sample, (1 BC-56) prepared in Example 6 was used in amounts of 18.8 mg for TG and 6.8 mg for DSC.

Figure 3:
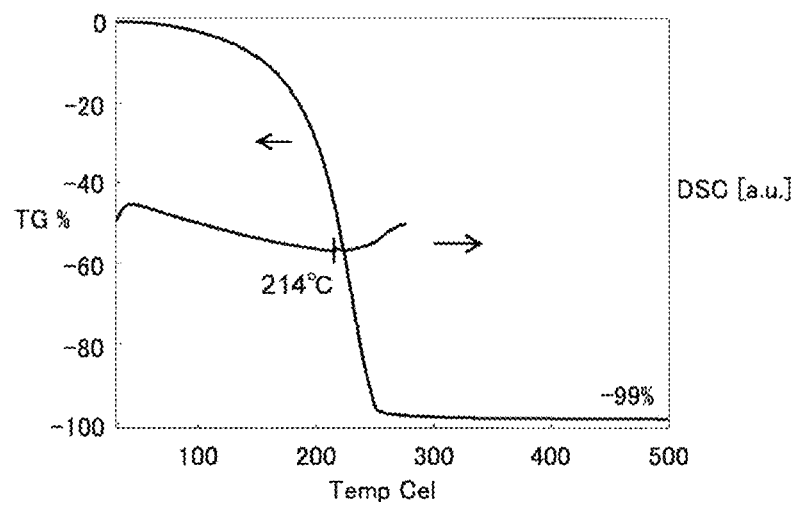
FIG. 3 is a TG and DSC chart of [(2-dimethylamino-1,1-dimethylethyl)(trimethylsilyl)amino](2,2,6,6-tetramethyl-3,5-heptanedionate) cobalt (1 BC-56) in Evaluation Example 2.

The results of TG measured in an atmosphere in which argon flowed at 400 mL/min at a temperature-raising rate of 10° C./min, and the results of DSC measured in a sealed container at a temperature-raising rate of 10° C./min are shown in FIG. 3. It is found from TG that the residue by thermal decomposition is 1% and from DSC that the thermal decomposition starting temperature is 214° C. Further, no melting point measured in DSC proves that (1 BC-56) is liquid at room temperature.

Comparative Example 1

Thermal Analysis of bis[(2-dimethylamino-1,1-dimethylethyl)(trimethylsilyl)amino] cobalt As a sample, bis[(2-dimethylamino-1,1-dimethylethyl)(trimethylsilyl)amino] cobalt prepared in Reference Example 7 was used in amounts of 19.0 mg for TG and 7.0 mg for DSC.

Figure 4:
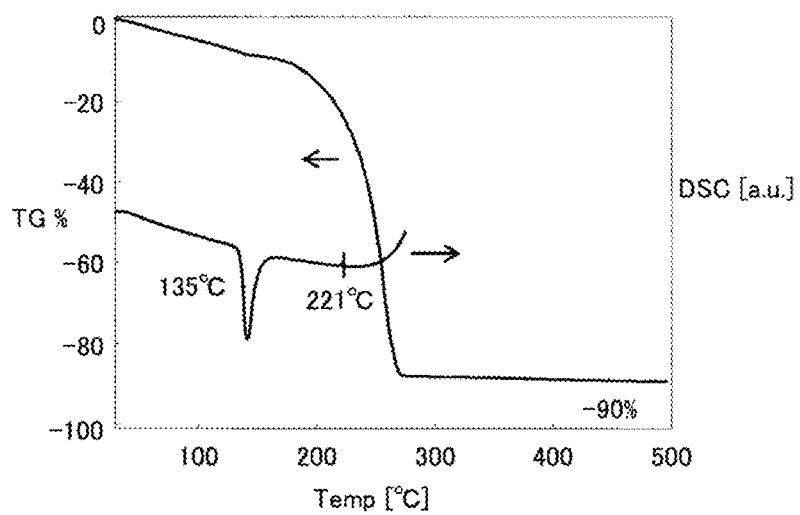
FIG. 4 is a TG and DSC chart of bis[(2-dimethylamino-1,1-dimethylethyl)(trimethylsilyl)amino] cobalt in Comparative Example 1.

The results of TG measured in an atmosphere in which argon flowed at 400 mL/min at a temperature-raising rate of 10° C./min, and the results of DSC measured in a sealed container at a temperature-raising rate of 10° C./min are shown in FIG. 4. It is found from TG that the residue by thermal decomposition is 10% and from DSC that the thermal decomposition starting temperature is 221° C. and the melting point is 135° C.

It is found from the results in Evaluation Examples 1 and 2 and Comparative Example 1 that the cobalt complex (1) has a very low melting point as compared with bis[(2-dimethylamino-1,1-dimethylethyl)(trimethylsilyl)amino] cobalt.

Comparative Example 2

Thermal Analysis of bis[(tert-butyl)(trimethylsilyl)amino] cobalt (2-2)

As a sample, (2-2) prepared in Reference Example 1 was used in amounts of 19.2 mg for TG and 3.6 mg for DSC.

Figure 5:
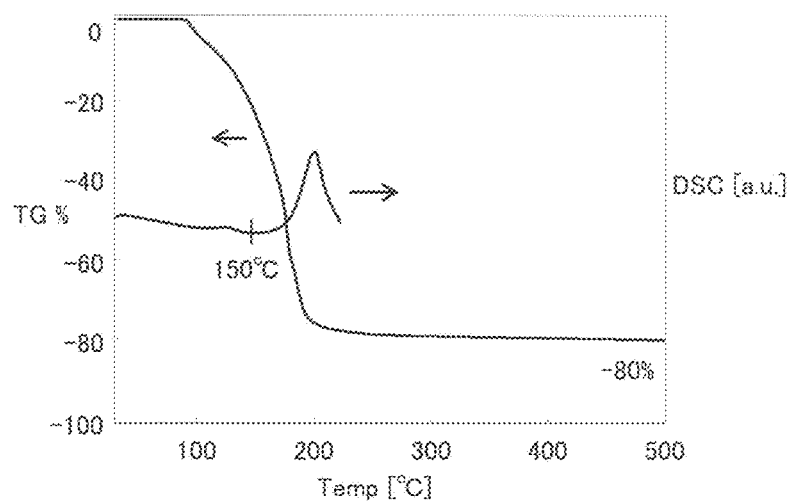
FIG. 5 is a TG and DSC chart of bis[(tert-butyl)(trimethylsilyl)amino] cobalt (2-2) in Comparative Example 2.

The results of TG measured in an atmosphere in which argon flowed at 400 mL/min at a temperature-raising rate of 10° C./min, and the results of DSC measured in a sealed container at a temperature-raising rate of 10° C./min are shown in FIG. 5. It is found from TG that the residue by thermal decomposition is 20% and from DSC that the thermal decomposition starting temperature is 150° C. Further, no melting point being observed in DSC proves that (2-2) is liquid at room temperature.

It is found from the results in Evaluation Examples 1 and 2 and Comparative Example 2 that (2-2) is liquid at room temperature, however, as compared with (1AB-14) and (1 BC-56), a large amount of residue is observed in TG, and the thermal decomposition starting temperature observed in DSC is low. It is found that the cobalt complex (1) is a material excellent in supply stability and thermal stability as compared with (2-2).

Example 8

Using [(2-dimethylamino-1,1-dimethylethyl)(trimethylsilyl)amino][bis(trimethylsilypamino] cobalt (1AB-14) prepared in Example 3 as a material, a cobalt-containing thin film was produced by thermal CVD method. The apparatus used for producing the thin film is schematically shown in FIG. 1. The thin film production conditions are as follows.

Carrier gas flow rate: 45 sccm, ammonia flow rate: 40 sccm, diluent gas flow rate: 115 sccm, substrate material: $SiO_2$, film deposition time: 60 min, reaction chamber total pressure: 1.3 kPa, material container temperature: 70° C., vapor pressure of material: 4.4 Pa, total pressure in material container: 3.7 kPa, material supply rate: 0.05 sccm, substrate temperature: 200° C. Argon was used as the carrier gas and the diluent gas. The produced thin film was analyzed by fluorescent X-ray analysis and as a result, characteristic X-rays attributable to cobalt were detected. The film thickness was 24 nm as calculated from the intensities of X-rays detected. The electrical property of the prepared cobalt-containing thin film was measured by a four-probe method, whereupon it was 159 μΩ·cm.

Example 9

Using [(2-dimethylamino-1,1-dimethylethyl)(trimethylsilyl)amino](2,2,6,6-tetramethyl-3,5-heptanedionate) cobalt (1 BC-56) prepared in Example 6 as a material, a cobalt-containing thin film was produced by thermal CVD method. The apparatus used for producing the thin film is schematically shown in FIG. 1. The thin film production conditions are as follows.

Carrier gas flow rate: 30 sccm, ammonia flow rate: 100 sccm, diluent gas flow rate: 70 sccm, substrate material: $SiO_2$, film deposition time: 120 min, reaction chamber total pressure: 1.3 kPa, material container temperature: 85° C., vapor pressure of material: 13.3 Pa, total pressure in material container: 6.7 kPa, material supply rate: 0.06 sccm, substrate temperature: 200° C. Argon was used as the carrier gas and the diluent gas. The produced thin film was analyzed by fluorescent X-ray analysis and as a result, characteristic X-rays attributable to cobalt were detected. The film thickness was 54 nm as calculated from the intensities of X-rays detected. The electrical property of the prepared cobalt-containing thin film was measured by a four-probe method, whereupon it was 185 μΩ·cm.

Example 10

Using [(2-dimethylamino-1,1-dimethylethyl)(trimethylsilyl)amino](2,2,6,6-tetramethyl-3,5-heptanedionate) cobalt (1 BC-56) prepared in Example 6 as a material, a cobalt-containing thin film was produced by thermal CVD method. The apparatus used for producing the thin film is schematically shown in FIG. 1. The thin film production conditions are as follows.

Carrier gas flow rate: 30 sccm, ammonia flow rate: 100 sccm, hydrogen flow rate: 3 sccm, diluent gas flow rate: 67 sccm, substrate material: $SiO_2$, film deposition time: 120 min, reaction chamber total pressure: 1.3 kPa, material container temperature: 85° C., vapor pressure of material: 13.3 Pa, total pressure in material container: 6.7 kPa, material supply rate: 0.06 sccm, substrate temperature: 200° C.

Argon was used as the carrier gas and the diluent gas. The produced thin film was analyzed by fluorescent X-ray analysis and as a result, characteristic X-rays attributable to cobalt were detected. The film thickness was 98 nm as calculated from the intensities of X-rays detected. The electrical property of the prepared cobalt-containing thin film was measured by a four-probe method, whereupon it was 105 μΩ·cm.

Example 11

Using [(2-dimethylamino-1,1-dimethylethyl)(trimethylsilyl)amino](2,2,6,6-tetramethyl-3,5-heptanedionate) cobalt (1 BC-56) prepared in Example 6 as a material, a cobalt-containing thin film was produced by thermal CVD method. The apparatus used for producing the thin film is schematically shown in FIG. 1. The thin film production conditions are as follows.

Figure 6:
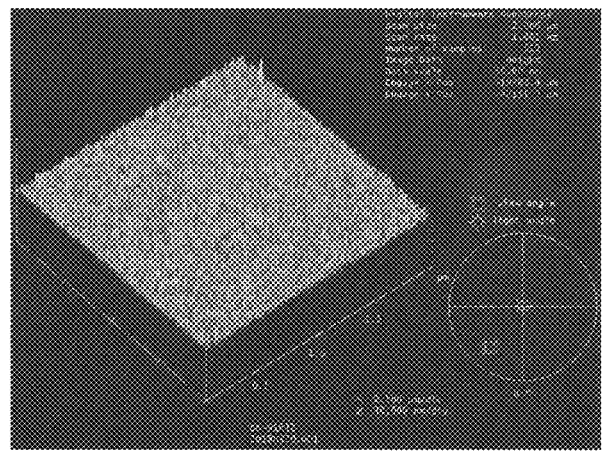
FIG. 6 is a diagram illustrating an AFM image of a film obtained in Example 11.

Carrier gas flow rate: 30 sccm, ammonia flow rate: 100 sccm, diluent gas flow rate: 70 sccm, substrate material: Ru, film deposition time: 15 min, reaction chamber total pressure: 1.3 kPa, material container temperature: 85° C., vapor pressure of material: 13.3 Pa, total pressure in material container: 6.7 kPa, material supply rate: 0.06 sccm, substrate temperature: 200° C. Argon was used as the carrier gas and the diluent gas. The produced thin film was analyzed by fluorescent X-ray analysis and as a result, characteristic X-rays attributable to cobalt were detected. The film thickness was 9 nm as calculated from the intensities of X-rays detected. The surface smoothness of the obtained film was evaluated by AFM, whereupon Ra of the film was 1.0 nm, and Rms was 1.4 nm (see FIG. 6)

Comparative Example 3

Using bis(N,N'-diisopropylacetoamidinate) cobalt (Co($^i$PrNC(Me)N$^i$Pr)$_2$) as the material, a cobalt-containing thin film was produced by thermal CVD method. The apparatus used for producing the thin film is schematically shown in FIG. 1. The thin film production conditions are as follows.

Carrier gas flow rate: 40 sccm, ammonia flow rate: 96 sccm, substrate material: SiO$_2$, film deposition time: 60 min, reaction chamber total pressure: 1.3 kPa, material container temperature: 91° C., vapor pressure of material: 40 Pa, total pressure in material container: 16 kPa, material supply rate: 0.1 sccm, substrate temperature: 200° C. Argon was used as the carrier gas, and no diluent gas was used. As a result of confirmation by fluorescent X ray analysis of the produced thin film, characteristic X-rays attributable to cobalt were detected. The film thickness was 6 nm as calculated from the intensities of X-rays detected. The electrical property of the prepared cobalt-containing thin film was measured by a four-probe method, whereupon it was at least $10^6$ μΩ·cm.

It is found from the results in Examples 8 to 11 and Comparative Example 3 that the cobalt complex (1) is a material capable of producing a cobalt-containing film excellent in surface smoothness having a low resistance, without using light or plasma in combination at low temperature of at most 200° C.

Example 12

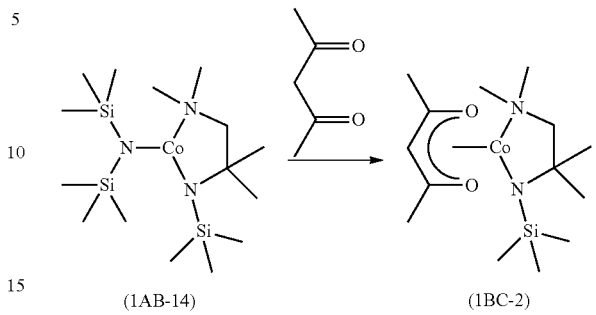

(1AB-14)          (1BC-2)

0.61 g (6.07 mmol) of acetylacetone was added at 0° C. to a THF (10 mL) solution of 2.47 g (6.07 mmol) of [(2-dimethylamino-1,1-dimethylethyl)(trimethylsilyl)amino][bis(trimethylsilypamino] cobalt (1AB-14) prepared in Example 3. The mixture was stirred at 25° C. for 17 hours, and the solvent was distilled off under reduced pressure. The remaining liquid was distilled (heating temperature: 110° C./back pressure: 54 Pa) to obtain 0.40 g (yield: 19%) of [(2-dimethylamino-1,1-dimethylethyl)(trimethylsilyl)amino](2,4-pentanedionate) cobalt (1 BC-2) as a dark green liquid.

$^1$H-NMR (400 MHz, C$_6$D$_6$, δ): 66.2 (br, 6H), 54.9 (br, 2H), 42.7 (br, 6H), 4.55 (br, 9H), 2.26 (br, 6H), −0.01 (br, 1H).

Example 13

Using [(2-dimethylamino-1,1-dimethylethyl)(trimethylsilyl)amino](2,2,6,6-tetramethyl-3,5-heptanedionate) cobalt (1 BC-56) prepared in Example 6 as a material, a cobalt-containing thin film was produced by thermal CVD method. The apparatus used for producing the thin film is schematically shown in FIG. 1. The thin film production conditions are as follows.

Carrier gas flow rate: 30 sccm, formic acid flow rate: 0.2 sccm, diluent gas flow rate: 166 sccm, substrate material: Ru, film deposition time: 120 min, reaction chamber total pressure: 1.3 kPa, material container temperature: 85° C., vapor pressure of material: 13.3 Pa, total pressure in material container: 6.7 kPa, material supply rate: 0.06 sccm, substrate temperature: 200° C. Argon was used as the carrier gas and the diluent gas. The produced thin film was analyzed by fluorescent X-ray analysis and as a result, characteristic X-rays attributable to cobalt were detected. The film thickness was 49 nm as calculated from the intensities of X-rays detected. The element composition of the prepared film was quantitatively determined by X-ray photoelectron spectroscopy (ESCA).

C: 6 atm %, N: 0 atm %, O: 1 atm %, Si: 0 atm %, Co: 93 atm %.

Example 14

Using [(2-dimethylamino-1,1-dimethylethyl)(trimethylsilyl)amino](2,2,6,6-tetramethyl-3,5-heptanedionate) cobalt (1 BC-56) prepared in Example 6 as a material, a cobalt-containing thin film was produced by thermal CVD method. The apparatus used for producing the thin film is schematically shown in FIG. 1. The thin film production conditions are as follows.

Carrier gas flow rate: 30 sccm, formic acid flow rate: 0.2 sccm, diluent gas flow rate: 166 sccm, substrate material: Cu, film deposition time: 120 min, reaction chamber total pressure: 1.3 kPa, material container temperature: 85° C., vapor pressure of material: 13.3 Pa, total pressure in material container: 6.7 kPa, material supply rate: 0.06 sccm, substrate temperature: 200° C. Argon was used as the carrier gas and the diluent gas. The produced thin film was analyzed by fluorescent X-ray analysis and as a result, characteristic X-rays attributable to cobalt were detected. The film thickness was 49 nm as calculated from the intensities of X-rays detected.

Example 15

Using [(2-dimethylamino-1,1-dimethylethyl)(trimethylsilyl)amino](2,2,6,6-tetramethyl-3,5-heptanedionate) cobalt (1 BC-56) prepared in Example 6 as a material, a cobalt-containing thin film was produced by thermal CVD method. The apparatus used for producing the thin film is schematically shown in FIG. 1. The thin film production conditions are as follows.

Carrier gas flow rate: 30 sccm, formic acid flow rate: 0.2 sccm, diluent gas flow rate: 166 sccm, substrate material: Ta, film deposition time: 120 min, reaction chamber total pressure: 1.3 kPa, material container temperature: 85° C., vapor pressure of material: 13.3 Pa, total pressure in material container: 6.7 kPa, material supply rate: 0.06 sccm, substrate temperature: 200° C. Argon was used as the carrier gas and the diluent gas. The produced thin film was analyzed by fluorescent X-ray analysis and as a result, characteristic X-rays attributable to cobalt were detected. The film thickness was 44 nm as calculated from the intensities of X-rays detected.

Example 16

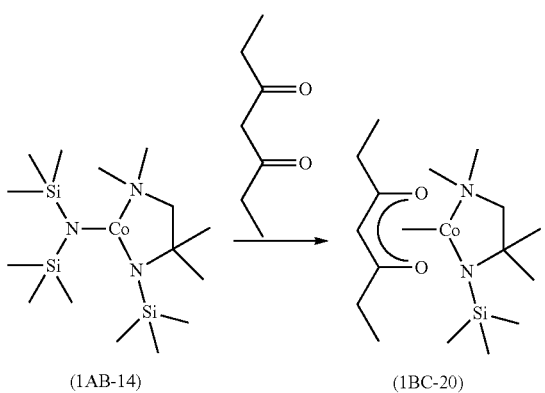

(1AB-14)  (1BC-20)

0.43 g (3.34 mmol) of heptane-3,5-dione was added at 0° C. to a THF (20 mL) solution of 1.36 g (3.34 mmol) of [(2-dimethylamino-1,1-dimethylethyl)(trimethylsilyl)amino][bis(trimethylsilypamino] cobalt (1AB-14) prepared in Example 3. The mixture was stirred at 25° C. for 16 hours, and the solvent was distilled off under reduced pressure. The remaining liquid was distilled (heating temperature: 130° C./back pressure: 56 Pa) to obtain 0.10 g (yield: 8%) of [(2-dimethylamino-1,1-dimethylethyl)(trimethylsilyl)amino](3,5-heptanedionate) cobalt (1 BC-20) as a dark green liquid.

$^1$H-NMR (400 MHz, $C_6D_6$, δ): 66.1 (br, 6H), 54.5 (br, 2H), 41.8-47.5 (br, 7H), 11.5 (brs, 6H), 9.71 (br, 4H), 4.46 (br, 9H).

Example 17

Figure 7:
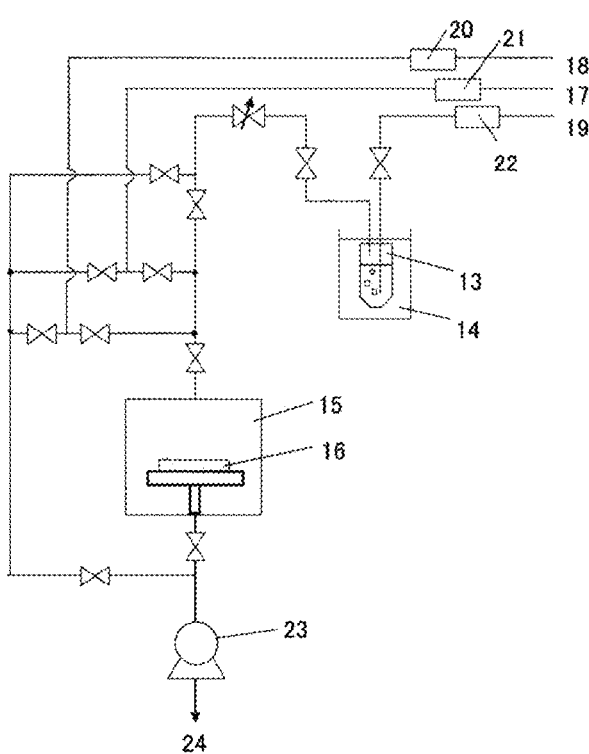
FIG. 7 is a diagram schematically illustrating an ALD apparatus used in Examples 17 and 18.

Using [(2-dimethylamino-1,1-dimethylethyl)(trimethylsilyl)amino](2,2,6,6-tetramethyl-3,5-heptanedionate) cobalt (1 BC-56) prepared in Example 6 as a material, a cobalt-containing thin film was produced by ALD method on a $SiO_2$ substrate. The apparatus used for producing the thin film is schematically shown in FIG. 7. The thin film production conditions are as follows.

A cycle comprising the following steps (1) to (4) was repeated 240 times totally for 120 minutes under conditions of carrier gas: argon 30 sccm, reactive gas: mixed gas comprising ammonia 100 sccm and argon 70 sccm, purge gas: argon 70 sccm, material container temperature: 85° C., vapor pressure of material: 13.3 Pa, total pressure in material container: 6.7 kPa, material supply rate: 0.06 sccm, substrate temperature: 300° C., and reaction chamber total pressure: at most 1.4 Pa.

(1) A vaporized material by bubbling is introduced into a reaction chamber and adsorbed in the surface of the substrate for 5 seconds.
(2) The unreacted material is removed by argon purging for 5 seconds.
(3) The above reactive gas is introduced into the reaction chamber for 10 seconds and is reacted with the material adsorbed in the surface of the substrate.
(4) The unreacted reactive gas and by-products are removed by argon purging for 10 seconds.

The produced thin film was analyzed by fluorescent X-ray analysis and as a result, characteristic X-rays attributable to cobalt were detected. The film thickness was 6 nm as calculated from the intensities of X-rays detected.

Example 18

Using [(2-dimethylamino-1,1-dimethylethyl)(trimethylsilyl)amino](2,2,6,6-tetramethyl-3,5-heptanedionate) cobalt (1 BC-56) prepared in Examples 6 as a material, a cobalt-containing thin film was produced by ALD method. As a substrate, a hole substrate covered with Ru, having a hole diameter of 150 nm, a hole depth of 1,000 nm and an aspect ratio of 1:6.7 was used.

The apparatus used for producing the thin film is schematically shown in FIG. 7. The thin film production conditions are as follows.

A cycle comprising the following steps (1) to (4) was repeated 240 times totally for 120 minutes under conditions of carrier gas: argon 30 sccm, reactive gas: mixed gas comprising ammonia 100 sccm and argon 70 sccm, purge gas: argon 70 sccm, material container temperature: 85° C., vapor pressure of material: 13.3 Pa, total pressure in material container: 6.7 kPa, material supply rate: 0.06 sccm, substrate temperature: 225° C., and reaction chamber total pressure: at most 1.4 Pa.

(1) A vaporized material by bubbling is introduced into a reaction chamber and adsorbed in the surface of the substrate for 5 seconds.
(2) The unreacted material is removed by argon purging for 5 seconds.
(3) The above reactive gas is introduced into the reaction chamber for 10 seconds and is reacted with the material adsorbed in the surface of the substrate.

(4) The unreacted reactive gas and by-products are removed by argon purging for 10 seconds.

The produced thin film was analyzed by fluorescent X-ray analysis and as a result, characteristic X-rays attributable to cobalt were detected. The cross-section TEM observation of the thin film produced was performed, whereupon the surface of the hole substrate was covered with a 10 nm cobalt film, and the step coverage was 89%.

Example 19

Using [(2-dimethylamino-1,1-dimethylethyl)(trimethylsilyl)amino][bis(trimethylsilyl)amino] cobalt (1AB-14) prepared in Example 3 as a material, a cobalt-containing thin film was produced by thermal CVD method. The apparatus used for producing the thin film is schematically shown in FIG. 1. The thin film production conditions are as follows.

Carrier gas flow rate: 30 sccm, ammonia flow rate: 100 sccm, diluent gas flow rate: 70 sccm, substrate material: Ru, film deposition time: 60 min, reaction chamber total pressure: 1.3 kPa, material container temperature: 70° C., vapor pressure of material: 6.7 Pa, total pressure in material container: 3.3 kPa, material supply rate: 0.06 sccm, substrate temperature: 200° C. Argon was used as the carrier gas and the diluent gas. The produced thin film was analyzed by fluorescent X-ray analysis and as a result, characteristic X-rays attributable to cobalt were detected. The film thickness was 27 nm as calculated form the intensities of X-rays detected.

Example 20

Using [(2-dimethylamino-1,1-dimethylethyl)(trimethylsilyl)amino][bis(trimethylsilypamino] cobalt (1AB-14) prepared in Example 3 as a material, a cobalt-containing thin film was produced by thermal CVD method. The apparatus used for producing the thin film is schematically shown in FIG. 1. The thin film production conditions are as follows.

Carrier gas flow rate: 30 sccm, ammonia flow rate: 100 sccm, diluent gas flow rate: 70 sccm, substrate material: $SiO_2$, film deposition time: 60 min, reaction chamber total pressure: 1.3 kPa, material container temperature: 70° C., vapor pressure of material: 6.7 Pa, total pressure in material container: 3.3 kPa, material supply rate: 0.06 sccm, substrate temperature: 150° C. Argon was used as the carrier gas and the diluent gas. The produced thin film was analyzed by fluorescent X-ray analysis and as a result, characteristic X-rays attributable to cobalt were detected. The film thickness was 14 nm as calculated form the intensities of X-rays detected. The electrical property of the prepared cobalt-containing thin film was measured by a four-probe method, whereupon it was 247 µΩ·cm.

Example 21

Using [(2-dimethylamino-1,1-dimethylethyl)(trimethylsilyl)amino][bis(trimethylsilypamino] cobalt (1AB-14) prepared in Example 3 as a material, a cobalt-containing thin film was produced by thermal CVD method. The apparatus used for producing the thin film is schematically shown in FIG. 1. The thin film production conditions are as follows.

Carrier gas flow rate: 30 sccm, ammonia flow rate: 100 sccm, diluent gas flow rate: 70 sccm, substrate material: Ru, film deposition time: 60 min, reaction chamber total pressure: 1.3 kPa, material container temperature: 70° C., vapor pressure of material: 6.7 Pa, total pressure in material container: 3.3 kPa, material supply rate: 0.06 sccm, substrate temperature: 150° C. Argon was used as the carrier gas and the diluent gas. The produced thin film was analyzed by fluorescent X-ray analysis and as a result, characteristic X-rays attributable to cobalt were detected. The film thickness was 20 nm as calculated form the intensities of X-rays detected.

Example 22

Using [(2-dimethylamino-1,1-dimethylethyl)(trimethylsilyl)amino][bis(trimethylsilypamino] cobalt (1AB-14) prepared in Example 3 as a material, a cobalt-containing thin film was produced by thermal CVD method. The apparatus used for producing the thin film is schematically shown in FIG. 1. The thin film production conditions are as follows.

Carrier gas flow rate: 30 sccm, formic acid flow rate: 0.4 sccm, diluent gas flow rate: 166 sccm, substrate material: $SiO_2$, film deposition time: 60 min, reaction chamber total pressure: 1.3 kPa, material container temperature: 70° C., vapor pressure of material: 1.0 Pa, total pressure in material container: 6.7 kPa, material supply rate: 0.02 sccm, substrate temperature: 100° C. Argon was used as the carrier gas and the diluent gas. The produced thin film was analyzed by fluorescent X-ray analysis and as a result, characteristic X-rays attributable to cobalt were detected. The film thickness was 5 nm as calculated from the intensities of X-rays detected.

Example 23

Using [(2-dimethylamino-1,1-dimethylethyl)(trimethylsilyl)amino][bis(trimethylsilypamino] cobalt (1AB-14) prepared in Example 3 as a material, a cobalt-containing thin film was produced by thermal CVD method. The apparatus used for producing the thin film is schematically shown in FIG. 1. The thin film production conditions are as follows.

Carrier gas flow rate: 30 sccm, formic acid flow rate: 0.4 sccm, diluent gas flow rate: 166 sccm, substrate material: Cu, film deposition time: 60 min, reaction chamber total pressure: 1.3 kPa, material container temperature: 70° C., vapor pressure of material: 1.0 Pa, total pressure in material container: 6.7 kPa, material supply rate: 0.02 sccm, substrate temperature: 100° C. Argon was used as the carrier gas and the diluent gas. The produced thin film was analyzed by fluorescent X-ray analysis and as a result, characteristic X-rays attributable to cobalt were detected. The film thickness was 5 nm as calculated from the intensities of X-rays detected.

Example 24

Using [(2-dimethylamino-1,1-dimethylethyl)(trimethylsilyl)amino][bis(trimethylsilypamino] cobalt (1AB-14) prepared in Example 3 as a material, a cobalt-containing thin film was produced by thermal CVD method. The apparatus used for producing the thin film is schematically shown in FIG. 1. The thin film production conditions are as follows.

Carrier gas flow rate: 30 sccm, ammonia flow rate: 100 sccm, hydrogen flow rate: 3 sccm, dipivaloylmethane flow rate: 0.06 sccm, substrate material: Ru, film deposition time: 60 min, reaction chamber total pressure: 0.7 kPa, material container temperature: 70° C., vapor pressure of material: 6.7 Pa, total pressure in material container: 3.3 kPa, material supply rate: 0.06 sccm, substrate temperature: 225° C. Argon was used as the carrier gas and the diluent gas. The produced thin film was analyzed by fluorescent X-ray analysis and as a result, characteristic X-rays attributable to cobalt were detected. The film thickness was 35 nm as calculated from the intensities of X-rays detected.

Example 25

Using [(2-dimethylamino-1,1-dimethylethyl)(trimethylsilyl)amino][bis(trimethylsilypamino] cobalt (1AB-14) prepared in Example 3 as a material, a cobalt-containing thin film was produced by thermal CVD method. The apparatus used for producing the thin film is schematically shown in FIG. 1. The thin film production conditions are as follows.

Carrier gas flow rate: 30 sccm, ammonia flow rate: 100 sccm, hydrogen flow rate: 3 sccm, dipivaloylmethane flow rate: 0.06 sccm, substrate material: W, film deposition time: 60 min, reaction chamber total pressure: 0.7 kPa, material container temperature: 70° C., vapor pressure of material: 6.7 Pa, total pressure in material container: 3.3 kPa, material supply rate: 0.06 sccm, substrate temperature: 225° C. Argon was used as the carrier gas and the diluent gas. The produced thin film was analyzed by fluorescent X-ray analysis and as a result, characteristic X-rays attributable to cobalt were detected. The film thickness was 39 nm as calculated from the intensities of X-rays detected.

The entire disclosures of Japanese Patent Application No. 2018-212049 filed on Nov. 12, 2018, Japanese Patent Application No. 2019-22221 filed on Feb. 12, 2019 and Japanese Patent Application No. 2019-132379 filed on Jul. 18, 2019 including specifications, claims, drawings and summaries are incorporated herein by reference in their entireties.

REFERENCE SYMBOLS

1: material container, 2: constant temperature chamber, 3: reaction chamber, 4: substrate, 5: reactive gas introduction port, 6: diluent gas introduction port, 7: carrier gas introduction port, 8: mass flow controller, 9: mass flow controller, 10: mass flow controller, 11: oil-sealed rotary vacuum pump, 12: evacuation, 13: material container, 14: constant temperature chamber, 15: reaction chamber, 16: substrate, 17: reactive gas introduction port, 18: reactive gas introduction port, 19: carrier gas introduction port, 20: mass flow controller, 21: mass flow controller, 22: mass flow controller, 23: oil-sealed rotary vacuum pump, 24: evacuation

The invention claimed is:

1. A cobalt complex represented by the following formula (1):

wherein $L^1$ and $L^2$ which are different from each other represent a unidentate amide ligand represented by the following formula (A), a bidentate amide ligand represented by the following formula (B) or a hetero atom-containing ligand represented by the following formula (C), wherein the cobalt complex is a liquid at room temperature, wherein $L^1$ is represented by the formula (A) or (C), and $L^2$ is represented by the formula (B):

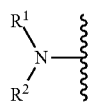

wherein $R^1$ and $R^2$ independently represent a $C_{1-6}$ alkyl group or a tri($C_{1-6}$ alkyl)silyl group, and the wave line represents a binding site to the cobalt atom;

wherein $R^3$ represents a tri($C_{1-6}$ alkyl)silyl group, $R^4$ and $R^5$ independently represent a $C_{1-4}$ alkyl group, and X represents a $C_{1-6}$ alkylene group;

wherein $R^6$ and $R^8$ independently represent a $C_{1-6}$ alkyl group, $R^7$ represents a hydrogen atom or a $C_{1-4}$ alkyl group, Y represents an oxygen atom or $NR^9$, Z represents an oxygen atom or $NR^{10}$, and $R^9$ and $R^{10}$ independently represent a $C_{1-6}$ alkyl group.

2. The cobalt complex according to claim 1, which is represented by the following formula (1AB):

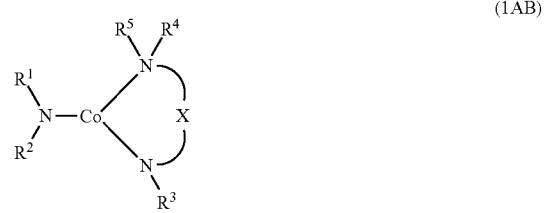

wherein $R^1$ and $R^2$ are as defined for $R^1$ and $R^2$ in the above formula (A), and $R^3$, $R^4$, $R^5$ and X are as defined for $R^3$, $R^4$, $R^5$ and X in the above formula (B).

3. The cobalt complex according to claim 2, wherein $R^1$, $R^2$ and $R^3$ are a tri($C_{1-4}$ alkyl)silyl group, $R^4$ and $R^5$ are a methyl group or an ethyl group, and X is a $C_{1-4}$ alkylene group.

4. The cobalt complex according to claim 2, wherein $R^1$, $R^2$ and $R^3$ are a trimethylsilyl group, $R^4$ and $R^5$ are a methyl group or an ethyl group, and X is a $C_{1-4}$ alkylene group.

5. A cobalt complex represented by the following formula (1AC):

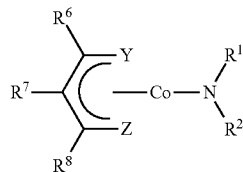
(1AC)

wherein the cobalt complex is a liquid at room temperature, wherein $R^1$ and $R^2$ independently represent a $C_{1-6}$ alkyl group or a tri($C_{1-6}$ alkyl)silyl group; and wherein $R^6$ and $R^8$ independently represent a $C_{1-6}$ alkyl group, $R^7$ represents a hydrogen atom or a $C_{1-4}$ alkyl group, Y represents an oxygen atom or $NR^9$, Z represents an oxygen atom or $NR^{10}$ and $R^9$ and $R^{10}$ independently represent a $C_{1-6}$ alkyl group.

6. The cobalt complex according to claim 5, wherein $R^1$ and $R^2$ are a tri($C_{1-4}$ alkyl)silyl group, $R^6$ and $R^8$ are a methyl group, $R^7$ is a hydrogen atom, Y is $NR^9$, Z is $NR^{10}$ and $R^9$ and $R^{10}$ are a $C_{1-4}$ alkyl group.

7. The cobalt complex according to claim 5, wherein $R^1$ and $R^2$ are a trimethylsilyl group, $R^6$ and $R^8$ are a methyl group, $R^7$ is a hydrogen atom, Y is $NR^9$, Z is $NR^{10}$, and $R^9$ and $R^{10}$ are a $C_{1-4}$ alkyl group.

8. The cobalt complex according to claim 1, which is represented by the following formula (1BC):

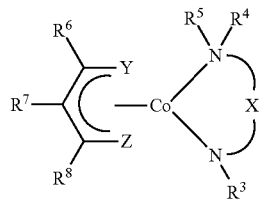
(1BC)

wherein $R^3$, $R^4$, $R^5$ and X are as defined for $R^3$, $R^4$, $R^5$ and X in the above formula (B), and $R^6$, $R^7$, $R^8$, Y and Z are as defined for $R^6$, $R^7$, $R^8$, Y and Z in the above formula (C).

9. The cobalt complex according to claim 8, wherein $R^3$ is a tri($C_{1-4}$ alkyl)silyl group, $R^4$ and $R^5$ are a methyl group or an ethyl group, X is a $C_{1-4}$ alkylene group, $R^6$ and $R^8$ are a $C_{1-4}$ alkyl group, $R^7$ is a hydrogen atom, and Y and Z are an oxygen atom.

10. The cobalt complex according to claim 8, wherein $R^3$ is a trimethylsilyl group, $R^4$ and $R^5$ are a methyl group or an ethyl group, X is a $C_{1-4}$ alkylene group, $R^6$ and $R^8$ are a $C_{1-4}$ alkyl group, $R^7$ is a hydrogen atom, and Y and Z are an oxygen atom.

11. A method for producing a cobalt complex represented by the following formula (1AB), which comprises reacting a bisamide complex represented by the following formula (2) and an aminoalkylamine represented by the following formula (3):

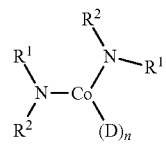
(2)

wherein $R^1$ and $R^2$ independently represent a $C_{1-6}$ alkyl group or a tri($C_{1-6}$ alkyl)silyl group, D represents a neutral ligand, and n represents 0 or 1;

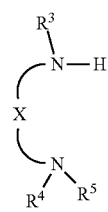
(3)

wherein $R^3$ represents a tri($C_{1-6}$ alkyl)silyl group, $R^4$ and $R^5$ independently represent a $C_{1-6}$ alkyl group, and X represents a $C_{1-6}$ alkylene group;

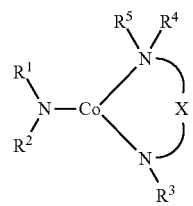
(1AB)

wherein $R^1$ and $R^2$ are as defined for $R^1$ and $R^2$ in the above formula (2), $R^3$, $R^4$, $R^5$ and X are as defined for $R^3$, $R^4$, $R^5$ and X in the above formula (3).

12. A method for producing the cobalt complex of claim 5, which comprises reacting a bisamide complex represented by the following formula (2) and a hetero atom-containing compound represented by the following formula (4) to provide the complex represented by the formula (1AC) of claim 5:

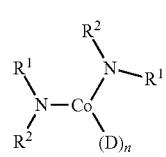
(2)

wherein $R^1$ and $R^2$ independently represent a $C_{1-6}$ alkyl group or a tri($C_{1-6}$ alkyl)silyl group, D represents a neutral ligand, and n represents 0 or 1:

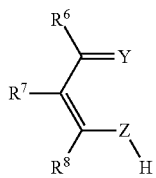

wherein $R^6$ and $R^8$ independently represent a $C_{1-6}$ alkyl group, $R^7$ represents a hydrogen atom or a $C_{1-4}$ alkyl group, Y represents an oxygen atom or $NR^9$, Z represents an oxygen atom or $NR^{10}$, and $R^9$ and $R^{10}$ independently represent a $C_{1-6}$ alkyl group.

13. A method for producing a cobalt complex represented by the following formula (1BC), which comprises reacting a cobalt complex represented by the following formula (1AB) and a hetero atom-containing compound represented by the following formula (4):

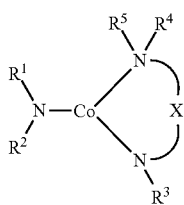

wherein $R^1$ and $R^2$ independently represent a $C_{1-6}$ alkyl group or a tri($C_{1-6}$ alkyl)silyl group, $R^3$ represents a tri($C_{1-6}$ alkyl)silyl group, $R^4$ and $R^5$ independently represent a $C_{1-4}$ alkyl group, and X represents a $C_{1-6}$ alkylene group;

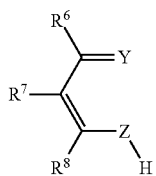

wherein $R^6$ and $R^8$ independently represent a $C_{1-6}$ alkyl group, $R^7$ represents a hydrogen atom or a $C_{1-4}$ alkyl group, Y represents an oxygen atom or $NR^9$, Z represents an oxygen atom or $NR^{10}$ and $R^9$ and $R^{10}$ independently represent a $C_{1-6}$ alkyl group;

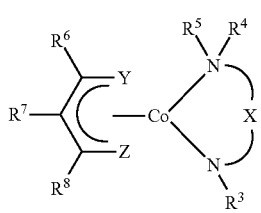

wherein $R^3$, $R^4$, $R^5$ and X are as defined for $R^3$, $R^4$, $R^5$ and X in the above formula (1AB), and $R^6$, $R^7$, $R^8$, Y and Z are as defined for $R^6$, $R^7$, $R^8$, Y and Z in the above formula (4).

14. A method for producing a cobalt-containing thin film, which comprises using a cobalt complex represented by the following formula (1) for a vapor deposition method based on a chemical reaction:

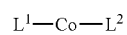

wherein $L^1$ and $L^2$ which are different from each other represent a unidentate amide ligand represented by the following formula (A), a bidentate amide ligand represented by the following formula (B) or a hetero atom-containing ligand represented by the following formula (C), wherein $L^1$ is represented by the formula (A) or (C), and $L^2$ is represented by the formula (B);

wherein $R^1$ and $R^2$ independently represent a $C_{1-6}$ alkyl group or a tri($C_{1-6}$ alkyl)silyl group, and the wave line represents a biding site to the cobalt atom;

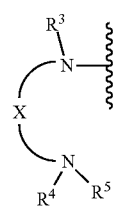

wherein $R^3$ represents a tri($C_{1-6}$ alkyl)silyl group, $R^4$ and $R^5$ independently represent a $C_{1-4}$ alkyl group, and X represents a $C_{1-6}$ alkylene group;

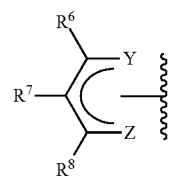

wherein $R^6$ and $R^8$ independently represent a $C_{1-6}$ alkyl group, $R^7$ represents a hydrogen atom or a $C_{1-4}$ alkyl group, Y represents an oxygen atom or $NR^9$, Z represents an oxygen atom or $NR^{10}$, and $R^9$ and $R^{10}$ independently represent a $C_{1-6}$ alkyl group.

15. The method for producing a cobalt-containing thin film according to claim 14, wherein the vapor deposition method based on a chemical reaction is a chemical vapor deposition method.

16. The method for producing a cobalt-containing thin film according to claim 14, wherein in the vapor deposition method based on a chemical reaction, a reactive gas is used.

17. The method for producing a cobalt-containing thin film according to claim 16, wherein a reducing gas is used as the reactive gas.

18. The method for producing a cobalt-containing thin film according to claim 14, wherein the cobalt-containing thin film is a metal cobalt thin film.

\* \* \* \* \*